*(12)* United States Patent
Gutin

(10) Patent No.: US 7,474,407 B2
(45) Date of Patent: Jan. 6, 2009

(54) OPTICAL COHERENCE TOMOGRAPHY WITH 3D COHERENCE SCANNING

(75) Inventor: Mikhail Gutin, Albany, NY (US)

(73) Assignees: Applied Science Innovations, Troy, NY (US); TTM Solutions, Albuquerque, NM (US)

( * ) Notice: Subject to any disclaimer, the term of this patent is extended or adjusted under 35 U.S.C. 154(b) by 575 days.

(21) Appl. No.: 10/546,421

(22) PCT Filed: Feb. 17, 2004

(86) PCT No.: PCT/US2004/004577

§ 371 (c)(1),
(2), (4) Date: Aug. 19, 2005

(87) PCT Pub. No.: WO2004/073501

PCT Pub. Date: Sep. 2, 2004

(65) Prior Publication Data

US 2006/0132790 A1    Jun. 22, 2006

Related U.S. Application Data

(60) Provisional application No. 60/448,777, filed on Feb. 20, 2003.

(51) Int. Cl.
*G01B 9/02* (2006.01)
(52) U.S. Cl. .................................................. 356/479
(58) Field of Classification Search .................. 356/479, 356/497, 478
See application file for complete search history.

(56) References Cited

U.S. PATENT DOCUMENTS 4,848,906 A    7/1989    Layton

| | | |
|---|---|---|
| 5,094,534 A | 3/1992 | Cole et al. |
| 5,202,745 A | 4/1993 | Sorin et al. |
| 5,257,991 A | 11/1993 | Fletcher et al. |
| 5,268,738 A | 12/1993 | Baney et al. |
| 5,268,741 A | 12/1993 | Chou et al. |
| 5,291,267 A | 3/1994 | Sorin et al. |
| 5,321,501 A | 6/1994 | Swanson et al. |
| 5,343,543 A | 8/1994 | Novak, Jr. et al. |
| 5,354,294 A | 10/1994 | Chou |

(Continued)

OTHER PUBLICATIONS

D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, Optical coherence tomography, Science 254, 1178-81, 1991.

(Continued)

*Primary Examiner*—Patrick J Connolly
(74) *Attorney, Agent, or Firm*—Jay R. Yablon

(57) ABSTRACT

Optical coherence tomography with 3D coherence scanning is disclosed, using at least three fibers (201, 202, 203) for object illumination and collection of backscattered light. Fiber tips (1, 2, 3) are located in a fiber tip plane (71) normal to the optical axis (72). Light beams emerging from the fibers overlap at an object (122) plane, a subset of intersections of the beams with the plane defining field of view (266) of the optical coherence tomography apparatus. Interference of light emitted and collected by the fibers creates a 3D fringe pattern. The 3D fringe pattern is scanned dynamically over the object by phase shift delays (102, 104) controlled remotely, near ends of the fibers opposite the tips of the fibers, and combined with light modulation. The dynamic fringe pattern is backscattered by the object, transmitted to a light processing system (108) such as a photo detector, and produces an AC signal on the output of the light processing system (108). Phase demodulation of the AC signal at selected frequencies and signal processing produce a measurement of a 3D profile of the object.

116 Claims, 12 Drawing Sheets

U.S. PATENT DOCUMENTS

| | | | |
|---|---|---|---|
| 5,361,130 A | 11/1994 | Kersey et al. | |
| 5,365,335 A | 11/1994 | Sorin | |
| 5,366,456 A | 11/1994 | Rink et al. | |
| 5,370,649 A | 12/1994 | Gardetto et al. | |
| 5,383,467 A | 1/1995 | Auer et al. | |
| 5,401,270 A | 3/1995 | Muller et al. | |
| 5,402,236 A | 3/1995 | Brown et al. | |
| 5,428,699 A | 6/1995 | Pon | |
| 5,434,669 A * | 7/1995 | Tabata et al. | 356/477 |
| 5,439,000 A | 8/1995 | Gunderson et al. | |
| 5,459,570 A | 10/1995 | Swanson et al. | |
| 5,465,147 A | 11/1995 | Swanson | |
| 5,490,521 A | 2/1996 | Davis et al. | |
| 5,495,541 A | 2/1996 | Murray et al. | |
| 5,509,917 A | 4/1996 | Cecchetti et al. | |
| 5,537,499 A | 7/1996 | Brekke | |
| 5,555,087 A | 9/1996 | Miyagawa et al. | |
| 5,562,657 A | 10/1996 | Griffin | |
| 5,570,182 A | 10/1996 | Nathel et al. | |
| 5,571,099 A | 11/1996 | Purcell, Jr. et al. | |
| 5,579,112 A | 11/1996 | Sugiyama et al. | |
| 5,601,087 A | 2/1997 | Gunderson et al. | |
| 5,633,712 A | 5/1997 | Venkatesh et al. | |
| 5,719,673 A | 2/1998 | Dorsel et al. | |
| 5,731,876 A | 3/1998 | Venkatesh et al. | |
| 5,740,291 A * | 4/1998 | De Lasa et al. | 385/31 |
| 5,772,657 A | 6/1998 | Hmelar et al. | |
| 5,835,642 A | 11/1998 | Gelikonov et al. | |
| 5,847,827 A | 12/1998 | Fercher | |
| 5,867,268 A | 2/1999 | Gelikonov et al. | |
| 5,920,390 A | 7/1999 | Farahi et al. | |
| 5,921,926 A | 7/1999 | Rolland et al. | |
| 5,975,697 A | 11/1999 | Podoleanu et al. | |
| 5,994,690 A | 11/1999 | Kulkarni et al. | |
| 6,002,480 A | 12/1999 | Izatt et al. | |
| 6,006,128 A | 12/1999 | Izatt et al. | |
| 6,010,449 A * | 1/2000 | Selmon et al. | 600/117 |
| 6,053,613 A | 4/2000 | Wei et al. | |
| 6,057,920 A | 5/2000 | Fercher et al. | |
| 6,069,698 A | 5/2000 | Ozawa et al. | |
| 6,091,496 A | 7/2000 | Hill | |
| 6,111,645 A | 8/2000 | Tearney et al. | |
| 6,124,930 A | 9/2000 | Fercher | |
| 6,134,003 A | 10/2000 | Tearney et al. | |
| 6,137,585 A | 10/2000 | Hitzenberger et al. | |
| 6,141,577 A | 10/2000 | Rolland et al. | |
| 6,144,449 A | 11/2000 | Knuettel et al. | |
| 6,160,826 A | 12/2000 | Swanson et al. | |
| 6,175,669 B1 | 1/2001 | Colston et al. | |
| 6,191,862 B1 | 2/2001 | Swanson et al. | |
| 6,198,540 B1 | 3/2001 | Ueda et al. | |
| 6,201,608 B1 | 3/2001 | Mandella et al. | |
| 6,233,055 B1 | 5/2001 | Mandella et al. | |
| 6,243,169 B1 | 6/2001 | Drabarek et al. | |
| 6,252,666 B1 | 6/2001 | Mandella et al. | |
| 6,252,669 B1 | 6/2001 | Drabarek | |
| 6,295,132 B1 | 9/2001 | Drabarek | |
| 6,307,633 B1 | 10/2001 | Mandella et al. | |
| 6,325,512 B1 | 12/2001 | Wei | |
| 6,381,023 B1 | 4/2002 | Kempe | |
| 6,381,490 B1 | 4/2002 | Ostrovsky | |
| 6,384,915 B1 | 5/2002 | Everett et al. | |
| 6,421,164 B2 | 7/2002 | Tearney | |
| 6,423,956 B1 * | 7/2002 | Mandella et al. | 359/215 |
| 6,441,356 B1 | 8/2002 | Mandella et al. | |
| 6,445,939 B1 | 9/2002 | Swanson et al. | |
| 6,456,769 B1 * | 9/2002 | Furusawa et al. | 385/117 |
| 6,466,713 B2 * | 10/2002 | Everett et al. | 385/31 |
| 6,485,413 B1 * | 11/2002 | Boppart et al. | 356/450 |
| 6,501,551 B1 | 12/2002 | Tearney et al. | |
| 6,507,747 B1 | 1/2003 | Gowda et al. | |
| 6,525,823 B1 | 2/2003 | Dogariu et al. | |
| 6,552,796 B2 | 4/2003 | Magnin et al. | |
| 6,552,797 B2 | 4/2003 | Swanson | |
| 6,556,854 B1 | 4/2003 | Sato et al. | |
| 6,559,950 B1 | 5/2003 | Dogariu et al. | |
| 6,564,087 B1 | 5/2003 | Pitris et al. | |
| 6,564,089 B2 | 5/2003 | Izatt et al. | |
| 6,587,206 B1 | 7/2003 | Dogariu et al. | |
| 6,590,664 B1 | 7/2003 | Dogariu et al. | |
| 6,608,684 B1 | 8/2003 | Gelikonov et al. | |
| 6,608,717 B1 | 8/2003 | Medford et al. | |
| 6,611,338 B1 | 8/2003 | Knuttel et al. | |
| 6,615,072 B1 | 9/2003 | Izatt et al. | |
| 6,618,152 B2 | 9/2003 | Toida | |
| 6,628,401 B2 | 9/2003 | Toida | |
| 6,636,755 B2 | 10/2003 | Toida | |
| 6,654,630 B2 | 11/2003 | Zuluaga et al. | |
| 6,657,727 B1 | 12/2003 | Izatt et al. | |
| 7,242,833 B2 * | 7/2007 | Yang et al. | 385/117 |
| 7,274,717 B1 * | 9/2007 | Minden et al. | 385/43 |

OTHER PUBLICATIONS

J. E. George, S. Golowich, P. F. Kolesar, A. J. Ritger, and M. Yang, Laser Optimized Multimode Fibers for Short Reach 10 Gbps Systems, National Fiber Optic Engineers Conference, 2001 Technical Proceedings, pp. 351-361.

M. D. Kulkarni, C. W. Thomas, and J. A. Izatt, Image enhancement in optical coherence tomography using deconvolution, Electron. Lett., vol. 33, pp. 1365-1367, 1997.

N. G. Chen, Q. Zhu, Rotary mirror array for high-speed optical coherence tomography, Optics Letters, vol. 27 Issue 8 p. 607, Apr. 2002.

Y. Lu, H. Lei, Q. Pan, Z. Liu, G. L. Rempel, Holographic coherence tomography for measurement of three-dimensional refractive-index space, Optics Letters, vol. 27 Issue 13 p. 1102, Jul. 2002.

B. Povazay, K. Bizheva, A. Unterhuber, B. Hermann, H. Sattmann, A. F. Fercher, W. Drexler, A. Apolonski, W. J. Wadsworth, J. C. Knight, P. St. J. Russell, M. Vetterlein, E. Scherzer. Submicrometer axial resolution optical coherence tomography, Optics Letters, vol. 27 Issue 20 p. 1800, Oct. 2002.

G. Hausler, M. W. Lindner, "Coherence radar" and "spectra; radar"—new tools for dermatological diagnosis, J. Biomd. Opt. 3(1)21-31, 1998.

M. Akiba, K. P. Chan, N. Tanno, Full-field optical coherence tomography by two-dimensional heterodyne detection with a pair of CCD cameras, Optics Letters, vol. 28 Issue 10 p. 816, May 2003.

R. A. Leitgeb, C. K. Hitzenberger, A. F. Fercher, T. Bajraszewski, Phase-shifting algorithm to achieve high-speed long-depth-range probing by frequency-domain optical coherence tomography, Optics Letters, vol. 28 Issue 22 p. 2201, Nov. 2003.

M. A. Choma, C. Yang, J. A. Izatt., Instantaneous quadrature low-coherence interferometry with 3×3 fiber-optic couplers, Optics Letters, vol. 28 Issue 22 p. 2162, Nov. 2003.

M. Laubscher, L. Froehly, B. Karamata, R. P. Salath, T. Lasser, Self-referenced method for optical path difference calibration in low-coherence interferometry, Optics Letters, vol. 28 Issue 24 p. 2476, Dec. 2003.

P. Yu, L. Peng, M. Mustata, J. J. Turek, M. R. Melloch, D. D. Nolte, Time-dependent speckle in holographic optical coherence imaging and the health of tumor tissue, Optics Letters, vol. 29 Issue 1 p. 68, Jan. 2004.

Y. Zhang, M. Sato, N. Tanno, Resolution improvement in optical coherence tomography by optimal synthesis of light-emitting diodes, Optics Letters, vol. 26 Issue 4 p. 205, Feb. 2001.

S. Bourquin, P. Seitz, R. P. Salath, Optical coherence topography based on a two-dimensional smart detector array, Optics Letters, vol. 26 Issue 8 p. 512, Apr. 2001.

L. Vabre, A. Dubois, A. C. Boccara, Thermal-light full-field optical coherence tomography, Optics Letters, vol. 27 Issue 7 p. 530, Apr. 2002.

J. A. Izatt, M. D. Kulkarni, S. Yazdanfar, J. K. Barton, A. J. Welch, In vivo bidirectional Doppler flow imaging of picoliter blood volumes using optical coherence tomography, Optics Letters, 22(18), 1439-1441, 1997.

S. J. Matcher, M. Cope, D. T. Delpy, In vivo measurements of the wavelength dependence of tissue-scattering coefficients between 760 and 900 nm measured with time-resolved spectroscopy, Applied Optics, vol. 36, No. 1, pp. 386-396, 1997.

L. Giniunas, R. Danielius, R. Karkockas. Scanning Delay Line with a Rotating-Parallelogram Prism for Low-Coherence Interferometry, Applied Optics, vol. 38 Issue 34 p. 7076, Dec. 1999.

A. V. Zvyagin, I. Eix, D. D. Sampson, High-Speed, High-Sensitivity, Gated Surface Profiling with Closed-Loop Optical Coherence Topography, Applied Optics, vol. 41 Issue 11 p. 2179, Apr. 2002.

N. A. Riza, Z. Yaqoob, Submicrosecond Speed Optical Coherence Tomography System Design and Analysis by use of Acousto-Optics, Applied Optics, vol. 42 Issue 16 p. 3018, Jun. 2003.

A. Dubois, L. Vabre, A. C. Boccara, E. Beaurepaire, High-Resolution Full-Field Optical Coherence Tomography with a Linnik Microscope, Applied Optics, vol. 41 Issue 4 p. 805, Feb. 2002.

C. K. Hitzenberger, M. Sticker, R. Leitgeb, A. F. Fercher, Differential phase measurements in low-coherence interferometry without 2 pi ambiguity, Optics Letters, vol. 26 Issue 23 p. 1864, Dec. 2001.

Y. Yasuno, Y. Sutoh, M. Nakama, S. Makita, M. Itoh, T. Yatagai, M. Mori, Spectral interferometric optical coherence tomography with nonlinear b-barium borate time gating, Optics Letters, vol. 27 Issue 6 p. 403, Mar. 2002.

M. D. Kulkarni, J. A. Izatt, Digital signal processing in optical coherence tomography, Coherence domain optical methods in biomedical science and clinical applications, Proc. SPIE; vol. 2981, pp. 2-6, 1997.

P. Andretzky, M. W. Lindner, W. Michael, J. M. Herrmann, A. Schultz, M. Konzog, M. F. Kiesewetter, G. Hausler, Optical coherence tomography by spectral radar: dynamic range estimation and in-vivo measurements of skin, Proc. SPIE 3567, p. 78-87, 1999.

F. I. Feldchtein, G. V. Gelikonov, V. M. Gelikonov, R. V. Kuranov, A. M. Sergeev, N. Gladkova, A. V. Shakhov, N. M. Shakhova, L. B. Snopova, A. B. Terent'eva, E. V. Zagainova, Y. P. Chumakov, and I. A. Kuznetzova, Endoscopic applications of optical coherence tomography, Opt. Express 3, 257-70 1998.

U. Morgner, W. Drexler, F. X. Kartner, X. D. Li, C. Pitris, E. P. Ippen, J. G. Fujimoto, Spectroscopic Optical Coherence Tomography, Optics Letters, 25, 111-113, Jan. 15, 2000.

C. K. Hitzenberger, A. F. Fercher, Differential phase contrast in optical coherence tomography, Optics Letters, vol. 24 Issue 9 p. 622, May 1999.

A. M. Rollins, J. A. Izatt, Optimal interferometer designs for optical coherence tomography, Optics Letters, vol. 24 Issue 21 p. 1484, Nov. 1999.

S. Bourquin, V. Monterosso, P. Seitz, R. P. Salath. Video-rate optical low-coherence refelectometry based on a linear smart detector array, Optics Letters, vol. 25 Issue 2 p. 102, Jan. 2000.

A. V. Zvyagin, J. B. Fitzgerald, K. K. M. B. D. Silva, D. D. Sampson, Real-time detection technique for Doppler optical coherence tomography, Optics Letters, vol. 25 Issue 22 p. 1645, Nov. 2000.

Y. Yasuno, M. Nakama, Y. Sutoh, M. Itoh, T. Yatagai, M. Mori, Phase-resolved correlation and its application to analysis of low-coherence interferograms, Optics Letters, vol. 26 Issue 2 p. 90, Jan. 2001.

V. X. Yang, M. L. Gordon, B. Qi, J. Pekar, S. Lo, E. Seng-Yue, A. Mok, B. C. Wilson, and I. A. Vitkin, High speed, wide velocity dynamic range Doppler optical coherence tomography (Part I): System design, signal processing, and performance, Opt. Express 11, 794-809, 2003.

A. M. Rollins, M. D. Kulkarni, S. Yazdanfar, R. Ungarunyawee, J. A. Izatt, In vivo video rate optical coherence tomography, Optics Express, vol. 3, No. 6, pp. 219-229, 1998.

S. A. Boppart, W. Drexler, U. Morgner, F. Kartner, J. Fujimoto, Ultrahigh Resolution and Spectroscopic OCT Imaging of Cellular Morphology and Function, Proc. Inter-Institute Workshop on In Vivo Optical Imaging at the National Institutes Health. Ed. A. H. Gandjbakhche. Sept. 16-17, pp. 56-61, 1999.

D. L. Marks, A. L. Oldenberg, J. J. Reynolds, S. A. Boppart, Autofocus algorithm for dispersion correction in optical coherence tomography, Applied Optics 42:3038-3046, 2003.

G. J. Tearney,, S. A. Boppart, B. E. Bouma, M. E. Brezinski, N. J. Weissman, J. F. Southern, J. G. Fujimoto, Scanning single-mode fiber optic catheter-endoscope for optical coherence tomography, Opt Lett 21(7):543-545, 1996.

M. Laubscher, M. Ducros, B. Karamata, T. Lasser, R. Salathe, Video-rate three-dimensional optical coherence tomography. Optics Express, vol. 10 Issue 9 p. 429, May. 2002.

M. Lazebnik, D. L. Marks, K. Potgieter, R. Gillette, S. A. Boppart, Functional optical coherence tomography for detecting neural activity through scattering changes, Optics Letters, 28(14):1218-1220, 2003.

C. Vinegoni, J. S. Bredfeldt, D. L. Marks, S. A. Boppart., Nonlinear optical contrast enhancement for optical coherence tomography, Optics Express, vol. 12 Issue 2 p. 331, Jan. 2004.

Li, X., Boppart, S. A,, J. Van Dam, H. Mashimo, M. W. Mutinga, W. Drexler, M. Klein, C. Pitris, M. L. Krinsky, M. E. Brezinski, J. G. Fujimoto, Optical coherence tomography: advanced technology for the endoscopic imaging of Barrett's esophagus, Endoscopy 32:921-930, 2000.

A. L. Oldenburg, J. J. Reynolds, D. L. Marks, S. A. Boppart, Fast-Fourier-domain delay line for in vivo optical coherence tomography with a polygonal scanner, Apl. Opt., 42(22):4606, Aug, 2003.

V. X. Yang, M. L. Gordon, E. Seng-Yue, S. Lo, B. Qi, J. Pekar, A. Mok, B. C. Wilson, and I. A. Vitkin, High speed, wide velocity dynamic range Doppler optical coherence tomography (Part II): Imaging in vivo cardiac dynamics of Xenopus laevis, Opt. Express 11, 1650-1658, 2003.

S. H. Yun, G. J. Tearney, J. F. de Boer, N. Iftimia, B. E. Bouma, High-speed optical frequency-domain imaging, Optics Express, vol. 11 Issue 22 p. 2953, Nov. 2003.

A. V. Zvyagin, K. K. M. B. Dilusha Silva, S. A. Alexandrov, T. R. Hillman, J. J. Armstrong, T. Tsuzuki, D. D. Sampson, Refractive index tomography of turbid media by bifocal optical coherence refractometry, Optics Express, vol. 11 Issue 25 p. 3503, Dec. 2003.

S. H. Yun, G. J. Tearney, B. E. Bouma, B. H. Park, J. F. de Boer, High-speed spectral-domain optical coherence tomography at 1.3 μm wavelength, Optics Express, vol 11 Issue 26 p. 3598, Dec. 2003.

J. K. Barton, A. J. Welch, J. A. Izatt, Investigating pulsed dye laser-blood vessel interaction with color Doppler optical coherence tomography, Optics Express, 2, 251-256, 1998.

R. A. Leitgeb, C. K. Hitzenberger, A. F. Fercher, Performance of Fourier domain vs. time domain optical coherence tomography. Optics Express, vol. 11 Issue 8 p. 889, Apr. 2003.

Y. Wang, J. S. Nelson, Z. Chen, B. J. Reiser, R. S. Chuck, R. S. Windeler, Optimal wavelength for ultrahigh-resolution optical coherence tomography, Optics Express, vol. 11 Issue 12 p. 1411, Jun. 2003.

V. X. D. Yang, M. L. Gordon, S. J. Tang, N. E. Marcon, G. Gardiner, B. Qi, S. Bisland, E. Seng-Yue, S. Lo, J. Pekar, B. C. Wilson, I. A. Vitkin, High speed, wide velocity dynamic range Doppler optical coherence tomography, Optics Express, vol. 11 Issue 19 p. 2416, Sept. 2003.

C. K. Hitzenberger, P. Trost, P. W. Lo, Q. Zhou, Three-dimensional imaging of the human retina by high-speed optical coherence tomography, Optics Express, vol. 11 Issue 21 p. 2753, Oct. 2003.

Zysk. A., J. J. Reynolds, D. L. Marks, P. S. Carney, S. A. Boppart, Projected index computed tomography, Opt. Letters 28:701-703, 2003.

S. A. Boppart, W. Drexler, U. Morgner, F. X. Kartner, J. G. Fujimoto, Ultrahigh Resolution and Spectropscopic Optical Coherence Tomography Imaging of Cellular Morphology and Function, Proc. Inter-Institue Workshop on In Vivo Optical Imaging at the National Institutes of Health. Ed. Gandjbakhche AH. Sept. 16-17, pp. 56-61, 1999.

J. A. Izatt, M. D. Kulkarni, K. Kobayashi, M. V. Sivak, J. K. Barton and A. J. Welch, Optical Coherence Tomography for Biodiagnostics, Optics and Photonics News 8:41-47, 1997.

M. Akiba, K. P. Chan, N. Tanno, Real-Time, Micrometer Depth-Resolved Imaging by Low-Coherence Reflectometry and a Two- Dimensional Heterodyne Detection Technique, Jpn. J. Appl. Phys. vol. 39 (2000) pp. L 1194-L 1196.

I. Vitkin, J. Woolsey, B. Wilson, and R. Anderson, Optical and thermal characterization of natural (sepia officinalis) melanin, Photochemistry and Photobiology, vol. 59, pp. 455-462, 1994.

J. G. Fujimoto, M. E. Brezinski, G. J. Tearney,, S. A. Boppart, B. E. Bouma, M. R. Hee, J. F. Southern, E. A. Swanson, Optical Biopsy and imaging using optical coherence tomography, Nature Med 1(9):970-972, 1995.

J. G. Fujimoto, C. Pitris, S. A. Boppart, M. E. Brezinski, Optical Coherence Tomography: An Emerging Technology for Biomedical Imaging and Optical Biopsy, Neoplasia, vol. 2, Nos. 1-2, Jan.-Apr. 2000, pp. 9-25.

* cited by examiner

OPTICAL COHERENCE TOMOGRAPHY WITH 3D COHERENCE SCANNING

BACKGROUND OF THE INVENTION

This invention relates to optical coherence tomography (OCT), specifically to fiber OCT with coherence scanning in three dimensions.

OCT known in the prior art typically involves one-dimensional coherence gating (scanning) in what will be illustrated herein as the "z" dimension, combined with mechanical scanning in the two remaining "x" and "y" dimensions, to produce a 3D image of a scattering object The invention to be disclosed herein provides an OCT apparatus with coherence scanning in all three dimensions and a method for implementation of such a scanning.

The literature contains numerous papers regarding various types of OCT and related scanning. For example:

S. A. Boppart, W. Drexler, U. Morgner, F. Kartner, J. Fujimoto, *Ultrahigh Resolution and Spectroscopic OCT Imaging of Cellular Morphology and Function*, Proc. Inter-Institute Workshop on In Vivo Optical Imaging at the National Institutes Health. Ed. A. H. Gandjbakhche. September 16-17, pp. 56-61, 1999, describes OCT with the femtosecond Cr:Forsterite laser tunable over wavelengths from 1230 to 1270 nm, providing structurally resolved spectroscopic information.

S. A. Boppart, W. Drexler, U. Morgner, F. X. Kartner, J. G. Fujimoto, *Ultrahigh Resolution and Spectroscopic Optical Coherence Tomography Imaging of Cellular Morphology and Function*, Proc. Inter-Institute Workshop on In Vivo Optical Imaging at the National Institutes of Health. Ed. Gandjbakhche A H. September 16-17, pp. 56-61, 1999, describes endoscopic in vitro OCT of specimens of Barrett's esophagus.

J. G. Fujimoto, S. A. Boppart, C. Pitris, M. E. Brezinski, *Optical coherence tomography a new technology for biomedical imaging*, Japanese Journal of Laser Surgery and Medicine 20:141-168, 199; and J. G. Fujimoto, M. E. Brezinski, G. J. Tearney, S. A. Boppart, B. E. Bouma, M. R. Hee, J. F. Southern, E. A. Swanson, *Biomedical imaging and optical biopsy using optical coherence tomography*, Nature Med 1(9):970-972, 1995, describe OCT to non-excisionally evaluate tissue morphology using a catheter or an endoscope.

G. J. Tearney, S. A. Boppart, B. E. Bouma, M. E. Brezinski, N. J. Weissman, J. F. Southern, J. G. Fujimoto, *Scanning single-mode fiber optic catheter-endoscope for optical coherence tomography*, Opt Lett 21(7):543-545, 1996, describes an OCT catheter-endoscope for micrometer-scale, cross-sectional imaging in internal organ systems. A device with a diameter as small as 1.1 mm has been achieved, and imaging of in vitro human venous morphology is demonstrated. Like much of the prior art, OCT is supplemented with mechanical scanning.

M. Lazebnik, D. L. Marks, K. Potgieter, R. Gillette, S. A. Boppart, *Functional optical coherence tomography for detecting neural activity through scattering changes*, Optics Letters, 28(14):1218-1220, 2003, describes functional optical coherence tomography (fOCT) for neural imaging by detecting scattering changes during the propagation of action potentials through neural tissue.

D. L. Marks, A. L. Oldenburg, J. J. Reynolds, S. A. Boppart, *Autofocus algorithm for dispersion correction in optical coherence tomography*, Applied Optics 42:3038-3046, 2003, describes an autofocus algorithm for estimating the delay line and material dispersion from OCT reflectance data based on minimizing the Renyi entropy of the corrected axial-scan image, which is a contrast-enhancement criterion. This autofocus algorithm can be used in conjunction with a high-speed, digital-signal-processor-based OCT acquisition system for rapid image correction.

A. L. Oldenburg, J. J. Reynolds, D. L. Marks, S. A. Boppart, *Fast-Fourier-domain delay line for in vivo optical coherence tomography with a polygonal scanner*, Apl. Opt., 42(22):4606, August, 2003, describes in vivo optical coherence tomography using a Fourier-domain optical delay line constructed with a commercially available polygonal scanner.

Zysk. A., J. J. Reynolds, D. L. Marks, P. S. Carney, S. A. Boppart, *Projected index computed tomography*, Opt. Letters 28:701-703, 2003, describes optical coherence tomography with images taken from several view angles to determine a mapping of the refractive indices of the sample.

Li, X., Boppart, S. A, J. Van Dam, H. Mashimo, M. W. Mutinga, W. Drexler, M. Klein, C. Pitris, M. L. Krinsky, M. E. Brezinski, J. G. Fujimoto, *Optical coherence tomography: advanced technology for the endoscopic imaging of Barrett's esophagus*, Endoscopy 32:921-930, 2000, describes OCT technology with compact fiberoptic imaging probes that can be used as an adjunct to endoscopy for real-time image-guided evaluation of Barrett's esophagus. Linear and radial (mechanical) scan patterns have different advantages and limitations depending upon the application.

J. A. Izatt, M. D. Kulkarni, S. Yazdanfar, J. K. Barton, A. J. Welch, *In vivo bidirectional Doppler flow imaging of picoliter blood volumes using optical coherence tomography*, Optics Letters, 22(18), 1439-1441, 1997, describes OCT with flow detection based on Doppler effect.

J. K. Barton, J. A. Izatt, A. J. Welch, *Investigating pulsed dye laser-blood vessel interaction with color Doppler optical coherence tomography*, Optics Express 2, 251-256, 1998, describes OCT with flow detection based on Doppler effect J. A. Izatt, M. D. Kulkarni, K. Kobayashi, M. V. Sivak, J. K. Barton, and A. J. Welch, *Optical Coherence Tomography for Biodiagnostics*, Optics and Photonics News 8:41-47, 1997, describes application of OCT in diagnostics M. Laubscher, M. Ducros, B. Karamata, T. Lasser, R. Salathe, *Video-rate three-dimensional optical coherence tomography*. Optics Express, Vol. 10 Issue 9 Page 429, May 2002, describes three-dimensional optical coherence tomography (3D OCT) at video rate. A 58 by 58 smart-pixel detector array was employed. A sample volume of 210×210×80 m3 (corresponding to 58×58×58 voxels) was imaged at 25 Hz.

L. Vabre, A. Dubois, A. C. Boccara, *Thermal-light full-field optical coherence tomography*, Optics Letters, Vol. 27 Issue 7 Page 530, April 2002, describes OCT system based on a Linnik-type interference microscope, illuminated by a white-light thermal lamp.

A. Dubois, L. Vabre, A. C. Boccara, E. Beaurepaire, *High-Resolution Full-Field Optical Coherence Tomography with a Linnik Microscope*, Applied Optics, Vol. 41 Issue 4 Page 805, February 2002, describes an OCT system based on a Linnik interference microscope with high-numerical-aperture objectives. Lock-in detection of the interference signal is achieved in parallel on a CCD by use of a photoelastic birefringence modulator and full-field stroboscopic illumination with an infrared LED.

V. X. Yang, M. L. Gordon, B. Qi, J. Pekar, S. Lo, E. Seng-Yue, A. Mok, B. C. Wilson, and I. A. Vitkin, *High speed, wide velocity dynamic range Doppler optical coherence tomography (Part I): System design, signal processing, and performance*, Opt. Express 11, 794-809, 2003, describes improvements in real-time Doppler optical coherence tomography (DOCT), acquiring up to 32 frames per second at 250×512 pixels per image.

V. X. Yang, M. L. Gordon, E. Seng-Yue, S. Lo, B. Qi, J. Pekar, A. Mok, B. C. Wilson, and I. A. Vitkin, *High speed, wide velocity dynamic range Doppler optical coherence tomography (Part II): Imaging in vivo cardiac dynamics of Xenopus laevis*, Opt. Express 11, 1650-1658, 2003, describes DOCT that can detect changes in velocity distribution during heart cycles, measure the velocity gradient in the embryo, and distinguish blood flow Doppler signal from heart wall motions.

D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, *Optical coherence tomography*, Science 254, 1178-81, 1991, describes the principles of OCT.

F. I. Feldchtein, G. V. Gelikonov, V. M. Gelikonov, R. V. Kuranov, A. M. Sergeev, N. Gladkova, A. V. Shakhov, N. M. Shakhova, L. B. Snopova, A. B. Terent'eva, E. V. Zagainova, Y. P. Chumakov, and I. A. Kuznetzova, *Endoscopic applications of optical coherence tomography*, Opt. Express 3, 257-70 1998, describes application of an endoscopic OCT system in clinical experiments to image human internal organs.

C. Vinegoni, J. S. Bredfeldt, D. L. Marks, S. A. Boppart., *Nonlinear optical contrast enhancement for optical coherence tomography*, Optics Express, Vol. 12 Issue 2 Page 331, January 2004, describes interferometric technique for measuring Coherent Anti-Stokes Raman Scattering (CARS) and Second Harmonic Generation (SHG) signals. Heterodyne detection is employed to increase the sensitivity in both CARS and SHG signal detection.

P. Yu, L. Peng, M. Mustata, J. J. Turek, M. R. Melloch, D. D. Nolte, *Time-dependent speckle in holographic optical coherence imaging and the health of tumor tissue*, Optics Letters, Vol. 29 Issue 1 Page 68, January 2004, describes holographic optical coherence imaging acquiring en face images from successive depths inside scattering tissue.

S. H. Yun, G. J. Tearney, B. E. Bouma, B. H. Park, J. F. de Boer, *High-speed spectral-domain optical coherence tomography at 1.3 μm wavelength*, Optics Express, Vol. 11 Issue 26 Page 3598, December 2003, describes a high-speed spectral domain optical coherence tomography (SD-OCT) system capable of acquiring individual axial scans in 24.4 μs at a rate of 19,000 axial scans per second.

M. Laubscher, L. Froehly, B. Karamata, R. P. Salath, T. Lasser, *Self-referenced method for optical path difference calibration in low-coherence interferometry*, Optics Letters, Vol. 28 Issue 24 Page 2476, December 2003, describes a method for the calibration of optical path difference modulation in low-coherence interferometry. Spectrally filtering a part of the detected interference signal results in a high-coherence signal that encodes the scan imperfections and permits their correction.

A. V. Zvyagin, K. K. M. B. Dilusha Silva, S. A. Alexandrov, T. R. Hillman, J. J. Armstrong, T. Tsuzuki, D. D. Sampson, *Refractive index tomography of turbid media by bifocal optical coherence refractometry*, Optics Express, Vol. 11 Issue 25 Page 3503, December 2003, describes tomographic imaging of the refractive index of turbid media using bifocal optical coherence refractometry (BOCR). The technique, which is a variant of optical coherence tomography, is based on the measurement of the optical pathlength difference between two foci simultaneously present in a medium of interest.

M. A. Choma, C. Yang, J. A. Izatt, *Instantaneous quadrature low-coherence interferometry with 3 3 fiber-optic couplers*, Optics Letters, Vol. 28 Issue 22 Page 2162, November 2003, describes fiber-based quadrature low-coherence interferometers that exploit the inherent phase shifts of 33 and higher-order fiber-optic couplers.

R. A. Leitgeb, C. K. Hitzenberger, A. F. Fercher, T. Bajraszewski, *Phase-shifting algorithm to achieve high-speed long-depth-range probing by frequency-domain optical coherence tomography*, Optics Letters, Vol. 28 Issue 22 Page 2201, November 2003, describes how by exploiting the phase information of the recorded interferograms, it is possible to remove autocorrelation terms and to double the measurement range in OCT.

S. H. Yun, G. J. Tearney, J. F. de Boer, N. Iftimia, B. E. Bouma, *High-speed optical frequency-domain imaging*, Optics Express, Vol. 11 Issue 22 Page 2953, November 2003, describes high-speed, high-sensitivity, high-resolution optical imaging based on optical frequency-domain interferometry using a rapidly-tuned wavelength-swept laser.

C. K. Hitzenberger, P. Trost, P. W. Lo, Q. Zhou, *Three-dimensional imaging of the human retina by high-speed optical coherence tomography*, Optics Express, Vol. 11 Issue 21 Page 2753, October 2003, describes a technique that combines the transverse scanning approach of a confocal scanning laser ophthalmoscope with the depth sectioning capability of OCT. A stable high-frequency carrier is generated by use of an acousto optic modulator, and high frame rate is obtained by using a resonant (mechanical) scanning mirror for the priority scan (x-direction).

V. X. D. Yang, M. L. Gordon, S. J. Tang, N. E. Marcon, G. Gardiner, B. Qi, S. Bisland, E. Seng-Yue, S. Lo, J. Pekar, B. C. Wilson, I. A. Vitkin, *High speed, wide velocity dynamic range Doppler optical coherence tomography*, Optics Express, Vol. 11 Issue 19 Page 2416, September 2003, describes inhibition of the sidelobes of the axial point spread function in optical coherence tomography by shaping the power spectrum of the light source with a remaining power of 4.54 mW. A broadband amplified spontaneous emission source radiating at 156540 nm is employed in a free-space optical coherence tomography system.

N. A. Riza, Z. Yaqoob, *Submicrosecond Speed Optical Coherence Tomography System Design and Analysis by use of Acousto-Optics*, Applied Optics, Vol. 42 Issue 16 Page 3018, June 2003, describes a high-speed no-moving-parts optical coherence tomography (OCT) system that acquires sample data at less than a microsecond per data point sampling rate. The basic principle of the proposed OCT system relies on use of an acousto-optic deflector.

Y. Wang, J. S. Nelson, Z. Chen, B. J. Reiser, R. S. Chuck, R S. Windeler, *Optimal wavelength for ultrahigh-resolution optical coherence tomography*, Optics Express, Vol. 11 Issue 12 Page 1411, June 2003, describes the influence of depth dependent dispersion by the main component of biological tissues, water, on the resolution of OCT.

M. Akiba, K. P. Chan, N. Tanno, *Full-field optical coherence tomography by two-dimensional heterodyne detection with a pair of CCD cameras*, Optics Letters, Vol. 28 Issue 10 Page 816, May 2003, describes a two-dimensional heterodyne detection technique based on the frequency-synchronous detection method [Jpn. J. Appl. Phys. 39, 1194, 2000] which is demonstrated for full-field optical coherence tomography. This technique, which employs a pair of CCD cameras to detect the in-phase and quadrature components of the heterodyne signal simultaneously, offers the advantage of phase-drift suppression in interferometric measurement.

R. A. Leitgeb, C. K. Hitzenberger, A. F. Fercher, *Performance of Fourier domain vs. time domain optical coherence tomography*. Optics Express, Vol. 11 Issue 8 Page 889, April 2003, presents a discussion of noise sources in Fourier Domain Optical Coherence Tomography (FDOCT) setups.

The performance of FDOCT with charge coupled device (CCD) cameras is compared to current standard time domain OCT systems.

B. Povazay, K. Bizheva, A. Unterhuber, B. Hermann, H. Sattmann, A. F. Fercher, W. Drexler, A. Apolonski, W. J. Wadsworth, J. C. Knight, P. St. J. Russell, M. Vetterlein, E. Scherzer. *Submicrometer axial resolution optical coherence tomography,* Optics Letters, Vol. 27 Issue 20 Page 1800, October 2002, describes OCT with submicrometer axial resolution achieved by use of a photonic crystal fiber in combination with a sub-10-fs Tisapphire laser.

Y. Lu, H. Lei, Q. Pan, Z. Liu, G. L. Rempel, *Holographic coherence tomography for measurement of three-dimensional refractive-index space,* Optics Letters, Vol. 27 Issue 13 Page 1102, July 2002, describes a tomographic method for the measurement of three-dimensional refractive-index fields of transparent media, called holographic coherence tomography, which combines double-exposure holographic interferometry with the detecting style of optical coherence tomography. The three-dimensional refractive-index field can be achieved with a confocal lens system by continual longitudinal and horizontal scanning of the holographic reconstruction image.

N. G. Chen, Q. Zhu, *Rotary mirror array for high-speed optical coherence tomography,* Optics Letters, Vol. 27 Issue 8 Page 607, April 2002, describes a high-speed, high-duty-cycle, linear optical delay line suitable for optical coherence tomography and optical Doppler tomography. Periodic longitudinal scanning is achieved by use of a tilted mirror array rotating at a constant speed.

A. V. Zvyagin, I. Eix, D. D. Sampson, *High-Speed High-Sensitivity, Gated Surface Profiling with Closed-Loop Optical Coherence Topography,* Applied Optics, Vol. 41 Issue 11 Page 2179, April 2002, describes a surface profiling technique with a closed-loop optical coherence topography. This technique is a scanning beam, servo-locked variation of low-coherence interferometry.

Y. Yasuno, Y. Sutoh, M. Nakama, S. Makita, M. Itoh, T. Yatagai, M. Mori, *Spectral interferometric optical coherence tomography with nonlinear b-barium borate time gating,* Optics Letters, Vol. 27 Issue 6 Page 403, March 2002, describes a high-speed, all optical coherence tomography system. This tomography system employs spectral interferometry and optical Fourier transformation to reduce the number of mechanical scanning dimensions required for multidimensional profilometry.

C. K. Hitzenberger, M. Sticker, R. Leitgeb, A. F. Fercher, *Differential phase measurements in low-coherence interferometry without 2p ambiguity,* Optics Letters, Vol. 26 Issue 23 Page 1864, December 2001, describes a method that overcomes the ambiguity of quantitative phase measurements by low-coherence interferometry and optical coherence tomography due to restriction by the well-known 2 p ambiguity to path-length differences smaller than ½.

S. Bourquin, P. Seitz, R. P. Salath, *Optical coherence topography based on a two-dimensional smart detector array,* Optics Letters, Vol. 26 Issue 8 Page 512, April 2001, describes a low-coherence reflectometer based on a conventional Michelson interferometer and a novel silicon detector chip with a two-dimensional array of pixels that allows parallel heterodyne detection. Acquisition of three-dimensional images with more than 100,000 voxels per scan at a sensitivity of −58 dB and a rate of 6Hz is demonstrated.

Y. Zhang, M. Sato, N. Tanno, *Resolution improvement in optical coherence tomography by optimal synthesis of light-emitting diodes,* Optics Letters, Vol. 26 Issue 4 Page 205, February 2001, describes an approach to improving the longitudinal resolution of optical coherence tomography in free space, by optimal synthesis of several LED's.

Y. Yasuno, M. Nakama, Y. Sutoh, M. Itoh, T. Yatagai, M. Mori, *Phase-resolved correlation and its application to analysis of low-coherence interferograms,* Optics Letters, Vol. 26 Issue 2 Page 90, January 2001, describes a signal-processing technique that involves a phase-resolved correlation method to determine the phase distribution of low-coherence interferograms. This method improves the sensitivity and resolution of low-coherence interferometers.

A. V. Zvyagin, J. B. Fitzgerald, K. K. M. B. D. Silva, D. D. Sampson, *Real-time detection technique for Doppler optical coherence tomography,* Optics Letters, Vol. 25 Issue 22 Page 1645, November 2000, describes a detection technique, based on a modified electronic phase-locked loop, for Doppler optical coherence tomography. The technique permits real-time simultaneous reflectivity and continuous, bidirectional velocity mapping in turbid media over a wide velocity range with minimal sensitivity penalty compared with conventional optical coherence tomography.

S. Bourquin, V. Monterosso, P. Seitz, R. P. Salath. *Video-rate optical low-coherence reflectometry based on a linear smart detector array,* Optics Letters, Vol. 25 Issue 2 Page 102, January 2000, describes a low-coherence reflectometer based on a conventional Michelson interferometer and a novel silicon detector chip that allows parallel heterodyne detection. Cross-sectional images of 64256 pixels covering an area of 1.92 mm 1.3 mm are acquired at video rate and with a sensitivity close to the shot-noise limit.

L. Giniunas, R Danielius, R Karkockas. *Scanning Delay Line with a Rotating-Parallelogram Prism for Low-Coherence Interferometry,* Applied Optics, Vol. 38 Issue 34 Page 7076, December 1999, describes a fast scanning optical delay line for low-coherence interferometry that has good linearity, a high duty cycle, and a continuously adjustable scan range. The delay line consists of a rotating-parallelogram prism with the rotation axis tilted with respect to the incident beam and two motionless mirrors.

A. M. Rollins, J. A. Izatt, *Optimal interferometer designs for optical coherence tomography,* Optics Letters, Vol. 24 Issue 21 Page 1484, November 1999, describes a family of power-conserving fiber-optic interferometer designs for low-coherence reflectometry that use optical circulators, unbalanced couplers, and/or balanced heterodyne detection.

C. K. Hitzenberger, A. F. Fercher, *Differential phase contrast in optical coherence tomography,* Optics Letters, Vol.24 Issue 9 Page 622, May 1999, describes a modification of optical coherence tomography (OCT) that allows one to measure small phase differences between beams traversing adjacent areas of a specimen. The sample beam of a polarization-sensitive low-coherence interferometer is split by a Wollaston prism into two components that traverse the object along closely spaced paths.

Despite the wealth of literature in this area, none of these papers describes 3D coherence scanning. Most of them use mechanical scanning, one (Nabeel Riza) uses acousto-optical scanning (a straight replacement of a mechanical scanner by an AO one), or CCD-type 2D sensors which are not applicable for small, fiberoptic probes.

There are also a air number of U.S. patents dealing various aspect of OCT and related scanning, yet here too, 3D coherence scanning appears to be novel and inventive in relation to all of the prior art.

U.S. Pat. No. 6,325,512 discloses an OCT apparatus with eye tracking. U.S. Pat. No. 6,507,747 discloses an optical imaging probe for providing information representative of morphological arid biochemical properties of a sample. U.S.

Pat. No. 6,556,854 discloses a blood vessel imaging system using homodyne and heterodyne effects. U.S. Pat. No. 6,654,630 discloses a catheter based optical system for generating data as to the condition of a tissue sample of a mammalian vessel. U.S. Pat. No. 5,257,991 discloses a method and apparatus for directing light at an angle and provides an optical fiber with a beveled end. U.S. Pat. No. 5,343,543 discloses a side firing laser fiber. U.S. Pat. No. 5,354,294 discloses a fiber optic laser beam angle delivery. U.S. Pat. No. 5,361,130 discloses a fiber grating-based sensing system with interferometric wavelength-shift detection. U.S. Pat. No. 5,366,456 discloses an angle firing fiber optic laser. U.S. Pat. No. 5,370,649 discloses a laterally reflecting tip for laser transmitting fiber. U.S. Pat. No. 5,401,270 discloses an applicator device for laser radiation. U.S. Pat. No. 5,402,236 discloses a fiberoptic displacement sensor using interferometric techniques. U.S. Pat. No. 5,428,699 discloses a probe having optical fiber for laterally directing a laser beam. U.S. Pat. No. 5,439,000 discloses an apparatus for diagnosing tissue with a guidewire. U.S. Pat. No. 5,490,521 discloses an ultrasound biopsy needle. U.S. Pat. No. 5,495,541 discloses an optical delivery device with high numerical aperture curved waveguide. U.S. Pat. No. 5,509,917 discloses lensed caps for radial medical laser delivery devices. U.S. Pat. No. 5,537,499 discloses a side-firing laser optical fiber probe. U.S. Pat. No. 5,562,657 discloses a side firing laser catheter. U.S. Pat. No. 5,571,099 discloses a side firing optical probe. U.S. Pat. No. 5,601,087 discloses a guidewire and a fiber probe. U.S. Pat. No. 5,633,712 discloses a reflectometer for determining the thickness and index of refraction of a film. U.S. Pat. No. 5,772,657 discloses a side firing fiber optic laser probe. U.S. Pat. No. 6,091,496 discloses an apparatus for confocal interference microscopy using wavenumber domain reflectometry. U.S. Pat. No. 6,160,826 discloses a method and apparatus for performing optical frequency domain reflectometry using a tunable laser. U.S. Pat. No. 6,243,169 discloses an interferometric instrument for sensing the surfaces of a test object. U.S. Pat. No. 6,252,669 discloses an interferometric instrument provided with an arrangement for periodically changing a light path of a received beam component. U.S. Pat. No. 6,381,023 discloses an improved confocal microscope system which images sections of tissue utilizing heterodyne detection. U.S. Pat. No. 6,423,956 discloses an angled-dual-axis confocal scanning microscope comprising a fiber-coupled, angled-dual-axis confocal scanning head and a vertical scanning unit. U.S. Pat. No. 6,441,356 discloses an angled-dual-axis optical coherence scanning microscope comprising a fiber-coupled, high-speed angled-dual-axis confocal scanning head and a vertical scanning unit. U.S. Pat. No. 6,445,939 discloses ultra-small optical probes comprising a single-mode optical fiber and a lens which has substantially the same diameter as the optical fiber. U.S. Pat. No. 6,466,713 discloses the head of an optical fiber comprising the sensing probe of an optical heterodyne sensing device.

U.S. Pat. Nos. 6,525,823; 6,559,950; 6,587,206; and 6,590,664 all disclose an optical system for monitoring a colloidal suspension.

U.S. Pat. No. 5,094,534 discloses an optical layout similar to OCT, with the main purpose of measurement of displacement of a sensor diaphragm. However, no 3D image appears to be produced by the apparatus. U.S. Pat. No. 5,202,745 discloses a reflectometer with the layout similar to OCT. In the invention, modulation of phase by PZT appears serving to produce signal spectral component of the same frequency as a fixed filter frequency in a detector, for any given mirror velocity. No 3D image is formed.

U.S. Pat. No. 5,268,738 discloses a reflectometer with multiple reference planes for increased depth range. U.S. Pat. No. 5,268,741 discloses a reflectometer, bearing similarity to OCT. Modulation of the source is introduced for calibration. U.S. Pat. No. 5,291,267 discloses a reflectometer, with similarity to OCT, comprising an amplifier for better sensitivity and reduced measurement times. U.S. Pat. No. 5,365,335 discloses a reflectometer with similarity to OCT in the optical layout. U.S. Pat. No. 5,459,570 discloses an optical coherence domain reflectometer employing two or more wavelengths of light. Polarization sensitivity provides for measurement of birefringence. The apparatus employs modulation of light and a fixed filter. U.S. Pat. No. 5,719,673 discloses an apparatus for OCT characterization of a sample in a single spot. The specific application is for measuring properties of different layers in the eye.

U.S. Pat. No. 5,731,876 discloses a single spot OCT for measurement properties of layered films. U.S. Pat. No. 5,835,642 discloses an optical delay line with all-fiber design. U.S. Pat. No. 5,867,268 also discloses an optical delay line with all-fiber design. U.S. Pat. No. 6,111,645 discloses an optical delay line. U.S. Pat. No. 6,381,490 discloses an optical scanning and imaging system and related method for scanning and imaging an object. U.S. Pat. No. 6,564,087 discloses a fiberoptic needle probe, which involves mechanical rotation. U.S. Pat. No. 5,383,467 discloses a guidewire catheter and apparatus for diagnostic imaging. The apparatus is applicable to OCT and has a small probe diameter. U.S. Pat. No. 5,570,182 discloses an OCT apparatus with acousto-optic or PZT modulation for heterodyning. It includes a movable lens for mechanical scan in the two dimensions normal to the optical axis. U.S. Pat. No. 5,579,112 discloses a free space, non-fiberoptic, OCT apparatus. U.S. Pat. No. 5,847,827 discloses a conventional OCT apparatus where the axial (z) coordinate of the focal spot follows the coherence scan. U.S. Pat. No. 5,920,390 discloses an OCT apparatus with wavelength selectivity to characterize tissue based on the reflection spectrum. U.S. Pat. No. 5,921,926 discloses an OCT apparatus with simultaneous spectral interferometry capabilities. The design involves mechanical rotation of the fiber/lenslet array. U.S. Pat. No. 5,975,697 discloses an OCT apparatus with adjustable coherence properties and adjustable depth resolution. U.S. Pat. No. 6,006,128 discloses an OCT apparatus with Doppler flow imaging. U.S. Pat. No. 6,053,613 discloses a modified OCT interferometer. U.S. Pat. No. 6,057,920 discloses an OCT apparatus with focal spot z-position following the coherence scan. U.S. Pat. No. 6,069,698 discloses an OCT apparatus with light path adjusted by the uniaxial stage such that the beam interference is detected for the scan range, to ensure stable acquisition of tomographic images. The design involves mechanical motion of components.

U.S. Pat. No. 6,124,930 discloses an improvement on conventional OCT. The invention stabilizes frequency of the signal with a transverse scan. U.S. Pat. No. 6,137,585 discloses an apparatus for generating data representative of a three-dimensional distribution of the light backscattering potential of a transparent or semi-transparent object such as a human eye. The signal processing involves frequency shift by acousto-optical elements and heterodyning. One spot in the sample produces reference, another (moving) spot produces signal. This design decreases sensitivity to eye movement. U.S. Pat. No. 6,141,577 discloses an OCT apparatus with simultaneous spectral interferometry capabilities. The design involves mechanical rotation of the fiber/lenslet array. U.S. Pat. No. 6,175,669 discloses an optical coherence domain reflectometry guidewire with multiplexed fiber channels and both forward and side viewing. U.S. Pat. No. 6,191,862 discloses a conventional OCT apparatus with improved high-speed axial (z) scanning. U.S. Pat. No. 6,198,540 discloses an improved OCT apparatus with a plurality of reference planes, frequency-multiplexed, and high acquisition speed.

U.S. Pat. Nos. 6,201,608; 6,233,055; 6,252,666; and 6,307,633 all disclose an improved conventional OCT using a polarizing beam splitter and a polarization rotator to improve signal to noise ratio.

U.S. Pat. No. 6,384,915 discloses multiplexed optical coherence reflectometry with multiple fibers for guidance and viewing. U.S. Pat. No. 6,421,164 discloses a high speed conventional OCT apparatus with mechanical scanning. U.S. Pat. No. 6,485,413 discloses an imaging system for performing forward scanning imaging for application to therapeutic and diagnostic devises used in medical procedures. U.S. Pat. No. 6,501,551 discloses an imaging system for performing optical coherence tomography. The endoscopic device involves mechanical rotation and longitudinal scanning. U.S. Pat. No. 6,552,796 discloses a conventional OCT apparatus for reading information from a desired depth in a sample. U.S. Pat. No. 6,552,797 discloses an apparatus for measurement of the freezing point of substances. U.S. Pat. No. 6,564,089 discloses a conventional OCT apparatus with a Faraday rotator for stabilization of polarization and image contrast. U.S. Pat. No. 6,608,684 discloses an OCT apparatus with magnetic mechanical lateral scanning of a fiber. U.S. Pat. No. 6,608,717 discloses rapid in-vivo optical coherence microscopy with a conventional OCT layout. U.S. Pat. No. 6,615,072 discloses a conventional OCT apparatus with a Faraday rotator for stabilization of polarization and image contrast. U.S. Pat. No. 6,618,152 discloses an optical coherence tomography apparatus using optical-waveguide structure which reduces pulse width of low-coherence light frequency shift between reference and sample.

U S. Pat. No. 6,628,401 discloses an optical tomography imaging method and apparatus with amplified spontaneous emission light. This is yet another implementation of conventional OCT with mechanical scanning. U.S. Pat. No. 6,657,727 discloses interferometers for optical coherence domain reflectometry and optical coherence tomography using non-reciprocal optical elements. The design uses differential signal processing. It involves mechanical scanning, as in conventional OCT. U.S. Pat. No. 6,611,338 discloses an OCT apparatus using light of two wavelengths and amplitude modulation. The design involves mechanical scanning. U.S. Pat. No. 6,636,755 discloses a conventional OCT apparatus with high resolution for cellular imaging. The design requires mechanical scanning. U.S. Pat. No. 5,321,501 discloses a classic OCT apparatus by Fujimoto, et al. The apparatus requires 2D mechanical motion of either sample or the probe (part of the probe). U.S. Pat. No. 6,134,003 discloses an endoscopic OCT device, including a variety of probes. All embodiments involve mechanical motion.

U.S. Pat. No. 5,465,147 discloses an OCT apparatus. The 3D image of the sample is produced by a coherence scan in one (z) dimension and 2D (x,y) conventional imaging with a CCD. A drawback of the apparatus is the potentially low-frequency detection typical of CCD.

U.S. Pat. No. 5,994,690 discloses an OCT apparatus with deconvolution for improved axial resolution. The extent of resolution improvement was limited due to noise, as described in M. D. Kulkarni, C. W. Thomas, and J. A. Izatt, *Image enhancement in optical coherence tomography using deconvolution,* Electron. Lett., vol. 33, pp. 1365-1367, 1997.

U.S. Pat. No. 6002,480 discloses OCT with deconvolution, similar to U.S. Pat. No. 5,994,690.

U.S. Pat. No. 6,295,132 discloses a reflectometer with acousto-optical deflectors and gratings for transverse displacement of the beam. The device is inherently large and is not fiberoptic.

U.S. Pat. No. 5,555,087 discloses a 3D OCT apparatus employing a bundle of fibers, each producing the conventional OCT. The bundle replaces the mechanical 2D scan of other prior art such as in patents to Fujimoto and others. The drawbacks include large probe size, potentially slower operating with the CCD-type detector, and likely cross-talk between fibers producing artifacts in the output image.

We now proceed to a review of optical coherence tomography.

The basic layout of optical coherence tomography is shown in FIG. 1. A Light Source 110 has a low coherence length $L_c$, related to the spectral width $$\Delta\lambda : L_c \approx \frac{\lambda^2}{\Delta\lambda},$$

where $\lambda$ is central wavelength. $L_c$ is typically ~10 μm when super-luminescent diode serves as the light source. Typical instrumental function of the OCT is presented in FIG. 2.

The instrumental function (impulse response) is defined as the signal produced by scanning (displacement) of a reflector 116 on a photo detector 124 of FIG. 1 when the object 122 is a small point. The z-displacement 20 of the reflector 116 is scanned from the position when the optical path length from the light source 110 is exactly the same to the object 122 and to the reflector 116. The scanning range is typically comparable with the coherence length of the light source. An electromechanical device responsive to electromagnetic signals 118 such as but not limited to a piezoelectric stack is one possible means for causing reflector displacement 126, thereby introducing a phase delay. As the reflector is displaced, interference between the light scattered back from a point of object 122 and the light reflected by the reflector 116 produces z-fringes 142, As the displacement increases, the contrast of z-fringes 142 reduces due to loss of coherence (coherence gating). The width of the z-envelope 144 is defined by the coherence length $L_c$. Instrumental function, I (2l) defines the resolution in z (depth) as the depth is scanned by displacement of the reflector 116. Lateral scanning of the sample is done mechanically, by displacing either the sample or the beam in the x,y directions. Illustrated also are first 114 and second 120 focusing elements, and a 2×2 optical coupler/splitter 112. Lateral resolution is defined by the spot size produced by second focusing element 120.

Conventional OCT and existing commercial products based on the OCT principles outlined above register the z-envelope 144 of the signal ("envelope-only" measurement). The resolution of the depth measurement (imaging) in these tools is comparable to the coherence length $L_c$.

Enhancement of the z-resolution can be achieved if phase of the signal is measured. An analogy may be made with rangefinders, which have two major classes: those based on time-of-flight of a short radiation pulse and those based on the measurement of phase shifts of long pulses of radiation. Displacement 126 of the reference reflector 116 of a standard OCT setup (FIG. 1) is related to time in this analogy. The OCT measurement resolution-limited by the envelope of the signal is similar to the time-of-flight range measurement, whereas phase-shift measurements in range finding and phase demodulation in OCT have many similarities.

U.S. Pat. No. 5,994,690 discloses an OCT system with signal processing, including phase demodulation, to increase the resolution of depth measurement. The system performs deconvolution of the measured signal by Fourier transform of the measured signal, division by the Fourier transform of the impulse response (instrumental function), and an inverse Fourier transform. The impulse response is obtained by replacing the sample with a reflector and measuring the response of the system. The drawback of the method is the possible effect of spectral variation of scattering by the object. The result of deconvolution also strongly depends on the amount of noise and methods applied for its suppression. In experiments reported in M. D. Kulkarni, J. A. Izatt, *Digital signal processing in optical coherence tomography,* Coherence domain optical methods in biomedical science and clinical applications, Proc. SPIE; vol. 2981, pp. 2-6, 1997, an increase in resolution by a factor of slightly above 2 was achieved by deconvolution, whereas the number of carrier periods in the envelope was on the order of 10, the latter number being a reasonable expectation of gain in resolution with convolution in the absence of noise. OCT systems with improved signal to noise ratio (SNR) are of interest.

U. Morgner, W. Drexler, F. X. Kartner, X. D. Li, C. Pitris, E. P. Ippen, J. G. Fujimoto, *Spectroscopic Optical Coherence Tomography,* Optics Letters, 25, 111-113, Jan. 15, 2000, presents a new method for enhanced resolution and extraction of color information using a Mortlet wavelet transform. Along with spectral measurement at every object point, 1 μm longitudinal resolution was achieved.

A typical OCT system known in the art combines 1D coherence scanning and 2D mechanical scanning to produce a 3D profile of the sample. It appears that throughout the prior art, interferometric scanning is performed in one dimension of the sample only, typically designated as the "z" depth dimension. Transverse scanning is performed by mechanical displacement of either the sample, or the beam over the sample surface. In large systems using conventional optics, mechanical beam scanning is typically performed by a deflector such as a galvanometer. In small, fiber optic OCT systems, mechanical rotation of miniature optical elements is used. Such a system is disclosed in U.S. Pat. No. 6,445,939. Single-mode fibers and lenses with diameters substantially the same as the fibers are used in insertable medical devices, such as guidewires. The need for mechanical motion of elements at the tip of the fiber probe adds complexity and cost to the device, and may compromise its range of applications and reliability.

Conventional OCT systems and existing commercial products based on the OCT principle register the envelope of the signal ("envelope-only" measurement). The resolution of the depth measurement (imaging) in these tools is comparable to the coherence length $L_c$. As noted, for lateral x,y scanning today's "first generation" OCT instruments use mechanical systems to create cross-sectional images of the object. These instruments have several limitations, including:

Bulky probe tip
Slow operation
Limited depth of field
Limited speed of image acquisition
Rigid probe limiting the scope of applications
Large (mm) probe tip diameter, making the use of OCT problematic for many in-vivo imaging tasks
High cost of the OCT system
Low productivity and high cost of procedure It would be desirable to provide OCT systems with 3D imaging through optical fibers by 3D coherence gating and scanning, with no mechanical motion at the fiber tip.

It would also be desirable to provide a fiberoptic OCT imaging system applicable to inserted devices such as endoscopes, bronchoscopes, needles, and other similar tools.

It would also be desirable to provide a fiberoptic OCT system with low-cost, removable and disposable fiber probe attachment.

It would also be desirable to provide a new OCT system with improved signal to noise ratio.

Such a system would have many advantages, including:
Three-dimensional, in vivo imaging of tissues and cells in real time at video frame rates
3D coherence scanning with no probe mechanical motion
Focus-invariant imaging for extended depth of field
Improved, micron-level resolution for cellular imaging.
All-fiber, low cross-section, flexible probes—"b 3D Camera Through a Needle"
Low-cost, disposable probes
Affordable, compact, lightweight system
Image acquisition with improved signal-to-noise ratio (SNR) to enable micron and sub-micron imaging resolution

SUMMARY OF THE INVENTION

Disclosed herein is optical coherence tomography with 3D coherence scanning, employing an apparatus with three or more fibers for object illumination and collection of backscattered light. Probe tips of the fibers are located in a plane normal to the optical axis. Light beams emerging from the fibers overlap at an object plane, intersection of the beams with the plane defining field of view of the OCT system. Interference of light emitted and collected by the fibers creates a 3D fringe pattern. The 3D fringe pattern is scanned dynamically over the object by a combination of phase delays controlled remotely from near ends of the fibers opposite the probe tips of the fibers, and combined with light modulation. The dynamic fringe pattern is backscattered by the object, transmitted to the photo detector, and produces an AC signal on the output of the photo detector. Phase demodulation of the AC signal at selected frequencies and signal processing produce a measurement of a 3D profile of the object.

One embodiment of the invention is for a method and associated device comprising: a first optical fiber, comprising a first fiber tip thereof; a second optical fiber, comprising a second fiber tip thereof displaced from said first fiber tip substantially in a fiber tip plane substantially normal to an optical axis of said apparatus; and a phase delay $\phi_x$ module introducing a relative phase delay between said first optical fiber and said second optical fiber; wherein: adjustment of said phase delay $\phi_x$ module enables scanning of an object in a direction parallel to the displacement between said first fiber tip and said second fiber tip.

Another embodiment of the invention with corresponding special technical features is for a method and associated device comprising: a first optical fiber, comprising a first fiber tip thereof; a second optical fiber, comprising a second fiber tip thereof displaced from said first fiber tip substantially in a fiber tip plane substantially normal to an optical axis of said apparatus; a third optical fiber, comprising a third fiber tip thereof displaced from said first fiber tip and said second fiber tip substantially in said fiber tip plane, such that said first fiber tip, second fiber tip and third fiber tip define said fiber tip plane; a first modulator for modulation of light passed through said first optical fiber; a second modulator for modulation of light passed through said second optical fiber; a third modulator for modulation of light passed through said third optical fiber further; and a non-linear light processing system of at least of second power with respect to an intensity of light passed through said first modulator, said second modulator, and said third modulator, thereby producing a localized, 2-dimensional instrumental function.

A probe head with corresponding special technical features for use in connection with various embodiments of the invention is for a method and associated device comprising: a first optical fiber, comprising a first fiber tip thereof; a second optical fiber, comprising a second fiber tip thereof displaced from said first fiber tip substantially in a fiber tip plane substantially normal to an optical axis of said probe head; a third optical fiber, comprising a third fiber tip thereof displaced from said first fiber tip and said second fiber tip substantially in said fiber tip plane, such that said first fiber tip, second fiber tip and third fiber tip define said fiber tip plane; and an optical connector for connecting said probe head to and disconnecting said probe head from, said optical coherence tomography apparatus; wherein: said first fiber tip, said second fiber tip and said third fiber tip are configured such that light emitted therefrom substantially overlaps and is substantially unfocused at an intended distance of an object to be scanned from said first, second, and third fiber tips.

BRIEF DESCRIPTION OF THE DRAWINGS

The features of the invention believed to be novel are set forth in the appended claims. The invention, however, together with further objects and advantages thereof, may best be understood by reference to the following description taken in conjunction with the accompanying drawing(s) summarized below.

FIG. 17 schematically illustrates an embodiment comprising more than one low-coherence light source wherein the wavelengths of the sources are substantially similar.

DETAILED DESCRIPTION

Figure 3:
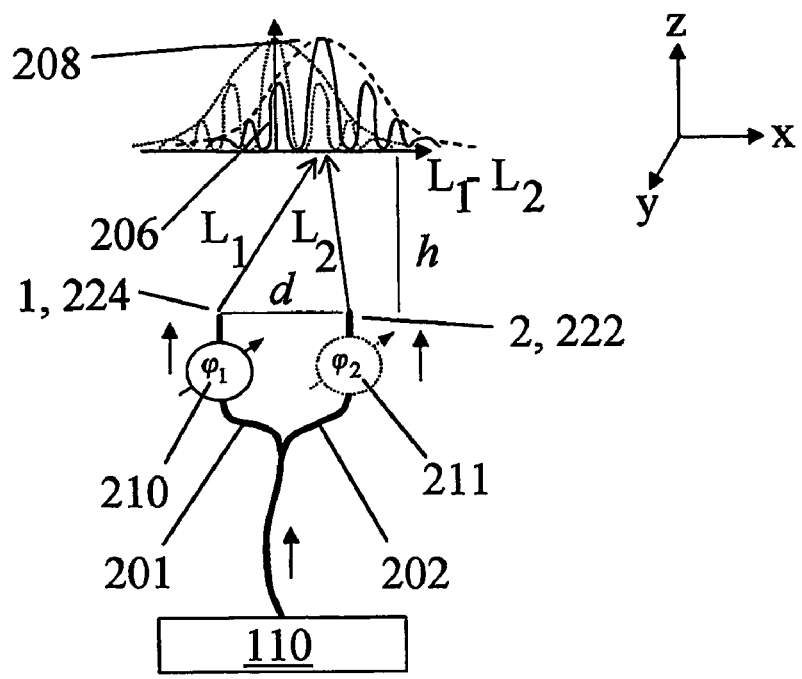
FIG. 3 is a schematic illustration of coherence transverse (x) scanning according to the present invention.

Disclosed herein is a new fiberoptic OCT system with coherence 3D scanning of an object 122 to be scanned. The concept is based on using multiple fibers for illumination and/or collection of light from a sample. Referring to FIG. 3, we begins by considering consider a first fiber 201 and a second fiber 202 of equal lengths connected to a common low-coherence light source 110, each emitting a diverging beam, so that there is an area where the beams overlap. In the area of overlap, interference of the beams will take place. A resulting x-fringe pattern 206 will vary in the x,y plane, normal to the regular OCT coherence scan in z-direction.

Figure 4:
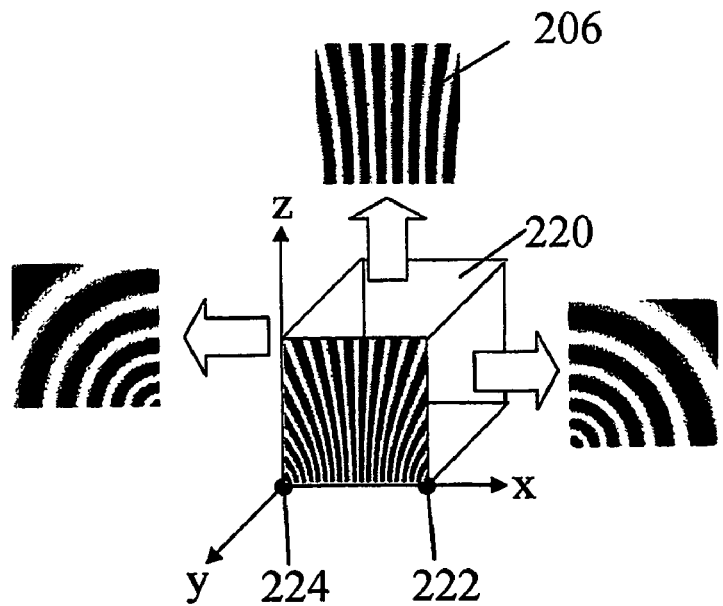
FIG. 4 is an illustration of a 3D interference pattern produced by two light sources.

FIG. 4 illustrates the 3D x-fringe pattern produced by light from these two fibers, which can be made by considering cross-sections of the pattern by sides of a cube 220, with the light sources (fiber tips 1 and 2) at two corners 222 and 224 along the x axis. The scale of the fringes is arbitrary and is chosen for illustration purposes only. For sources separated by a distance of ~100 wavelengths, the fringe pattern will have ~200 periods between the sources along the x-axis.

Figure 5:
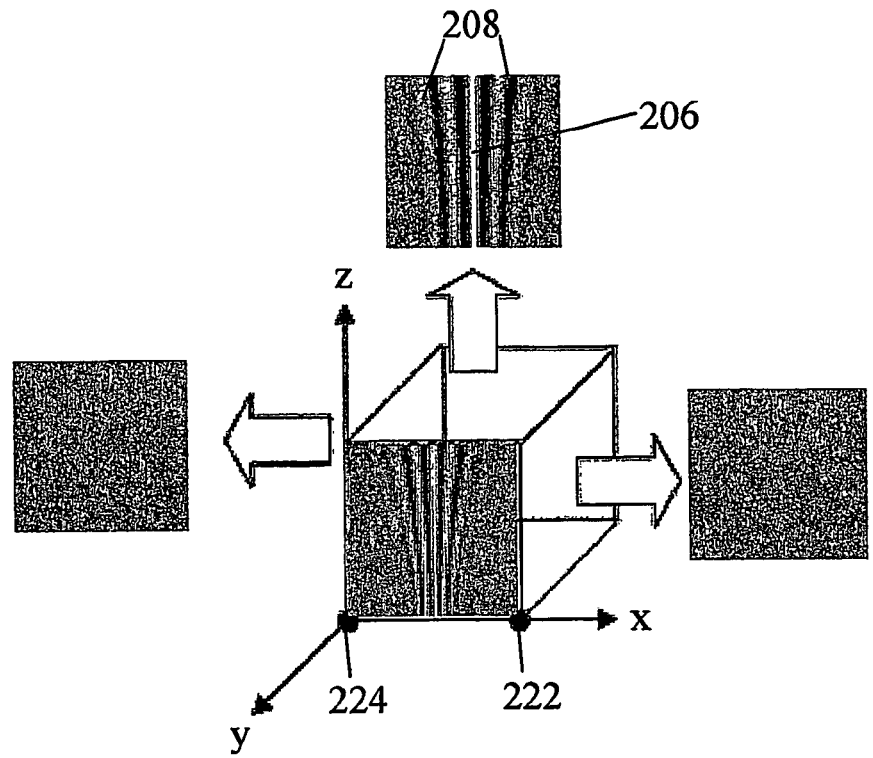
FIG. 5 is an illustration of coherence gating in 3D with low-coherence light.

The same interference pattern, with the effect of a finite coherence length light source, is shown in FIG. 5. The contrast of the interference pattern reduces as the optical path-length difference from the two sources at 222 and 224 to a point in the sample approaches the coherence length. This is similar to the effect of coherence length in the one-imensional case, as in the prior art OCT systems illustrated in FIGS. 1 and 2.

With this type of configuration, coherence gating becomes possible, selective in the transverse direction, along the x axis. As shown in FIG. 3, a phase delay $\phi_1$ module 210 introduced in fiber 201 and optionally a phase delay $\phi_2$ module 211 introduced in fiber 202 will shift the x-fringe pattern 206. Such a phase delay can be implemented by a variety of methods known in the art, including reflection from a movable reflector (116 and 118 in FIG. 1) as commonly done in conventional OCT. Examples of devices suitable for introducing a phase delay include PZT-mounted reflectors, fiber stretching devices, grating based delay lines, polygonal scanners, rotary mirror arrays, and any similar or equivalent devices known or which may become known in the art.

Both the carrier signal (x-fringe pattern 206) and the x-envelope 208 will shift if a relative phase delay between the two fibers is introduced. Periodic (e.g., saw-tooth) variation of the phase delay will result in a periodic scanning of the fringe pattern. Similar to z-scanning in conventional OCT, the controlled phase delay illustrated in FIG. 3 produces scanning in the x (or y) direction. The x-envelope 208 will scan as well, so that the relative phase of the x-fringe pattern 206 in the x-envelope 208 will stay unchanged. Intensity at a given point of the object 122 being scanned will experience modulation with the carrier frequency and varying amplitude (higher near the center of the x-envelope 208 and lower in the periphery).

Unlike in prior art, the transverse (x or y) coherence scanning can be performed by a remote control over the phases, at substantial distances from the fiber tips. This is important, because it eliminates the need for any mechanical scanning elements near the tips of the fibers. This makes the resulting probe device smaller, which is valuable for applications involving insertion into small areas, including endoscopy, colonoscopy, and optical biopsy. Additionally, a simple design of the fiber probe assembly makes possible its implementation as a low-cost, completely non-mechanical, removable probe head attachment 270 later illustrated in two embodiments in FIGS. 26 and 27, which may be disposable.

Figure 22:
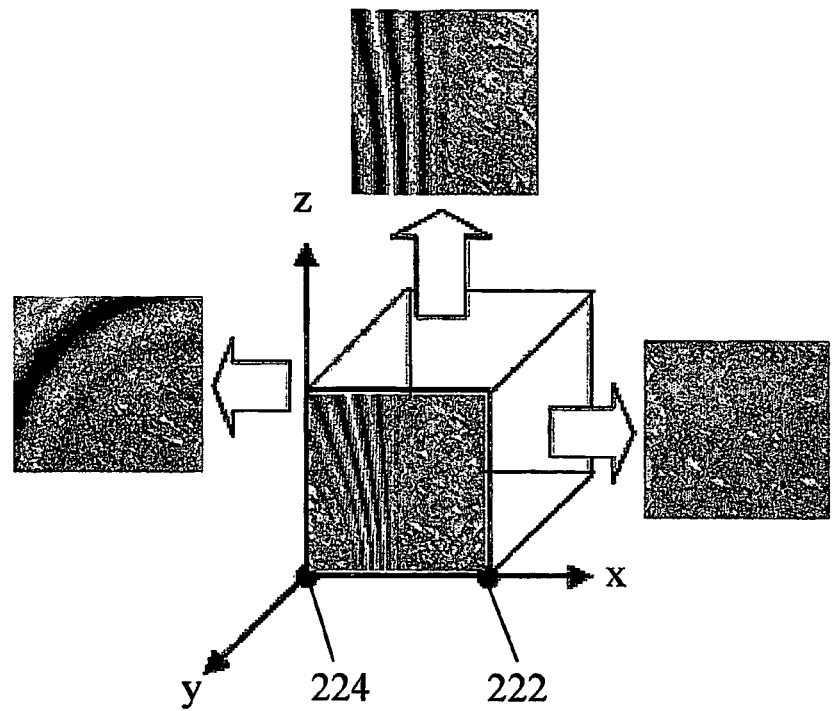
FIG. 22 is an illustration showing how interference patterns shift under a suitable phase delay.

FIG. 22 further illustrates how a phase delay introduced between the two light sources from fibers tips 1 and 2, as disclosed above, causes the interference pattern to shift. This should be contrasted with FIG. 5 showing the same patterns in the absence of the phase shift.

Figure 6:
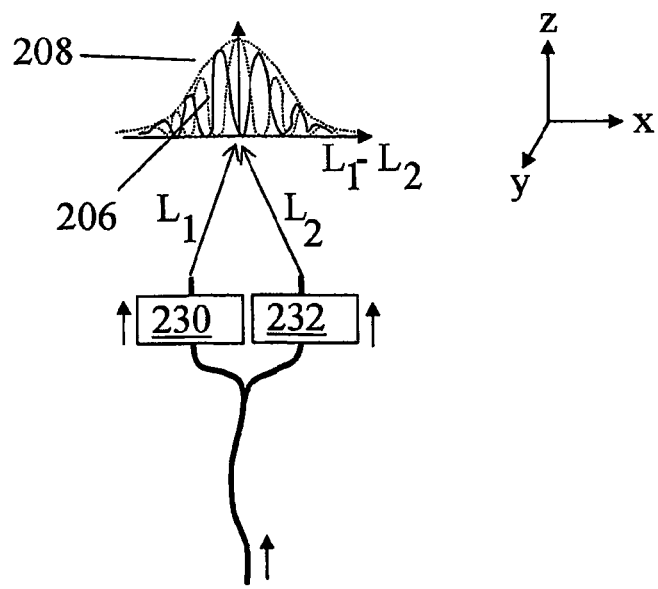
FIG. 6 is a schematic layout of transverse (x) coherence gating with modulation and "running carrier."

A second important aspect of the invention introduces amplitude modulation of the intensities in the fibers, using first and second modulators 230, 232, as shown in FIG. 6. For simplicity, FIG. 6 illustrates the effects of such a modulation without the aforementioned phase delays. Later, phase delay and modulation will be combined into one system along with non-linear signal processing. Appropriate modulators include, but are not limited to, acousto-optical modulators (AOM). Other amplitude modulators, such as, but not limited to, electro-optical, semiconductor, magneto-optic, fiberoptic, and similar or equivalent modulators known in the art or which may become known in the art can also be used. Phase modulation can also be used instead of amplitude modulation. The types of modules described above for introducing phase delay can also be used to provide such phase modulation. Other phase modulators can also be employed, such as, but not limited to, photo-elastic, electro-optical, semiconductor, fiberoptic, and other similar or equivalent devices known or which may become known in the art.

Optical spectrum of the modulated signal will contain, in addition to the optical frequency $v_{opt}$, additional frequencies $v_{opt}+f_{mod}$ and $v_{opt}-f_{mod}$. Due to interference of optical signals with slightly different frequencies (wavelengths), the interference pattern will contain components with moving fringes, so that intensity at a given point will oscillate with the frequency $f_{mod}$. The modulated light will have spectral components that create a moving fringe pattern 206, but the x-envelope 208 of the pattern will remain unchanged. That is, the phase delay discussed in connection with FIG. 3 moves the envelope 208 but leaves the fringe pattern 206 unchanged within the envelope; while the modulation introduced in FIG. 6 does not move the envelope 208 but does move the fringe pattern 206 with in the envelope. Deconvolution of the phase-demodulated signal produces the object profile in the x direction, similar to conventional OCT producing object profile in the z direction. The x and z profiles together provide for 2D coherence scanning.

Coherence scanning in both x and y directions can be produced if three fibers are used, resulting in a 3D fringe pattern illuminating the object 122. A possible layout is presented in FIG. 7. A first fiber 201 (with first fiber tip 1) and a second fiber 202 (with second fiber tip 2) are employed, with tips oriented along the x axis produce scanning in the x direction. A third fiber 203 (with third fiber tip 3) is placed with its tip oriented along the y axis relative first fiber tip 1. The interference pattern produced by the first (201) and the third (203) fibers, scanned as discussed above, will produce a scan in the y direction. One or more of the fibers 1, 2, 3 (201, 202, 203) is also used for conventional OCT measurement to produce a z-scan of the object. Combining these x and y coherence scans with conventional z coherence scans then results in a fully 3D coherence scan, without mechanical motion near the fiber tips.

Figure 7:
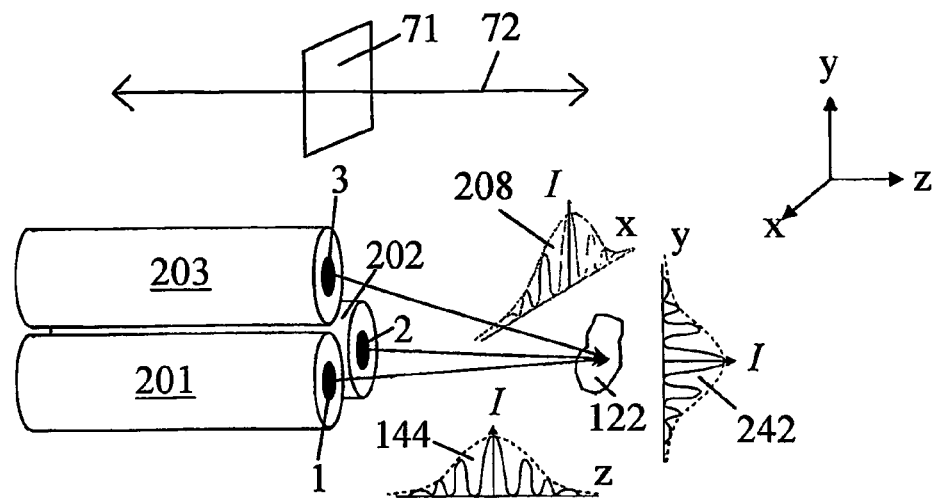
FIG. 7 is a perspective view of a fiber tip layout for two-dimensional transverse (relative to z) coherence scanning in x and y directions.

Note, while the second and third fibers 202, 203 form an approximately 90 degree angle relative to the first and second fibers 201, 202 in FIG. 7, that any configuration is possible so long as the tips of the three fibers define a fiber tip plane 71 substantially normal to the optical axis 72, i.e., so long as the three fiber tips do not all reside co-linearly along a single line normal to the optical axis 72. For example, not limitation, the three fibers might define the fiber tip plane 71 by forming an equilateral triangle, or an isosceles triangle, or, indeed, any sort of triangle. The details of the calculations to follow will then vary depending on the specific configuration chosen among the fiber tips, but in a way that will become apparent to someone of ordinary skill. The exemplary calculations to follow—and the general discussion to follow, for simplicity only—are based on the 90 degree angle (right triangle, with first fiber tip 1 opposite the hypotenuse) specifically illustrated in FIG. 7, with the clear understanding that other configurations are possible so long as the three fiber tips define a plane.

In general terms, FIG. 7 thus illustrates a first optical fiber 201, comprising a first fiber tip 1 thereof; a second optical fiber 202, comprising a second fiber tip 2 thereof displaced from said first fiber tip 1 substantially in a fiber tip plane 71 substantially normal to an optical axis 72 of said apparatus; and a third optical fiber 203, comprising a third fiber tip 3 thereof displaced from said first fiber tip 1 and said second fiber tip 2 substantially in said fiber tip plane 71, such that said first fiber tip 1, second fiber tip 2 and third fiber tip 3 define said fiber tip plane 71.

Figure 8:
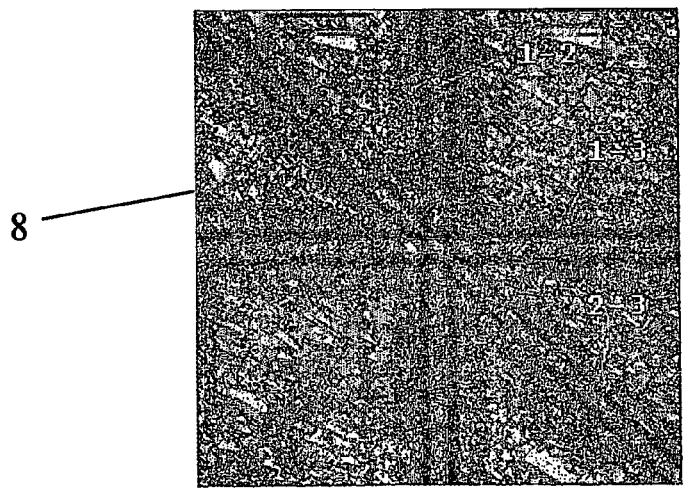
FIG. 8 illustrates a view of a low-coherence interference pattern produced by fibers in the layout of FIG. 7.

Referring to FIG. 7, interference patterns 208, 242, and 144 overlap in space to produce a 3D distribution of intensity. An x-y cross-section of this 3D fringe pattern 8 is shown in FIG. 8, illustrating the interference patterns between respective fiber tip pairs 1-2 (x), 1-3 (y), and 2-3 (z). The linear composition of this pattern is further illustrated in FIG. 23. Vertical fringes result from interference of light emitted by fiber tips 1 and 2 horizontal fringes result from fiber tips 1 and 3, and diagonal fringes result from fiber tips 2 and 3.

Figure 23:
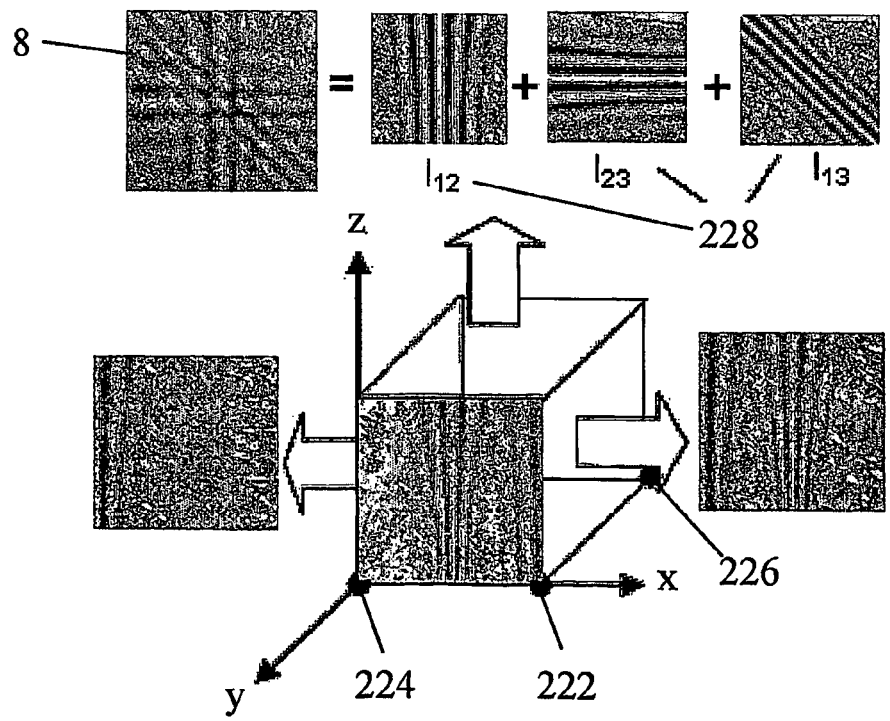
FIG. 23 is an illustration of a 3-dimensional interference pattern, without localization of the instrumental function, further illustrating the component patterns which contribute to the overall pattern of FIG. 8.

This may be further visualized by referring to FIG. 23. With the addition of a third source 226, partially coherent with sources 224 and 222, the interference pattern becomes more complex. This pattern is now a sum of three interference patterns: $I_{12}(x, y, z)$, $I_{23}(x, y, z)$, and $I_{13}(x, y, z)$, produced by pairs of sources (224, 222), (222, 226), and (224, 226), respectively. The component interference patterns 228 which result in the composite pattern 8 of FIGS. 8 and 23 are also illustrated. The pattern is not yet localized in space as would be desirable for imaging 3D scattering media by scanning the interference pattern in three dimensions. However, as will be shown later, additional signal processing can produce a localized instrumental function, and the phase delays discussed above can be used for non-mechanical scanning over the volume of the sample. Specifically, the signal processing will produce instrumental function equal to the product of component patterns $I_{12}(x, y, z)$ and $I_{23}(x, y, z)$.

Figure 9:
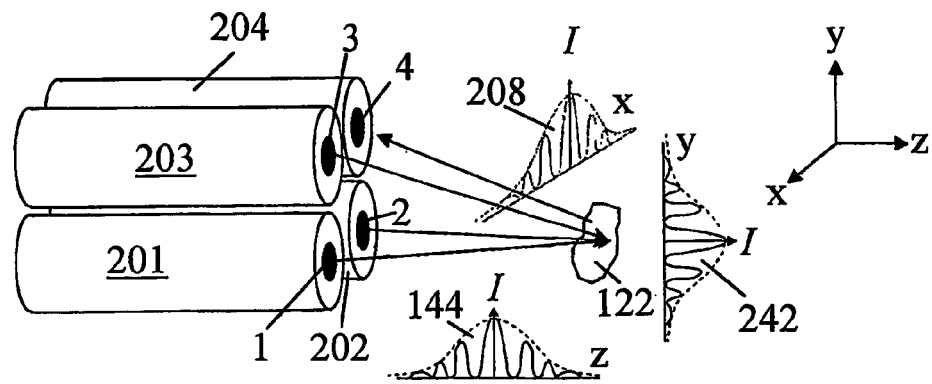
FIG. 9 is a perspective view of fiber tips layout for coherence scanning in x and y directions by three fibers, similar to FIG. 7, and scattered light collection by a fourth fiber.

Collection of light can be performed by one of the fibers 201, 202, or 203, or, alternatively, by a fourth, collection fiber 204 with a fourth fiber tip 4, as illustrated in FIG. 9, which shows the detail of fiber tips near the sample (object) 122.

Figure 10:
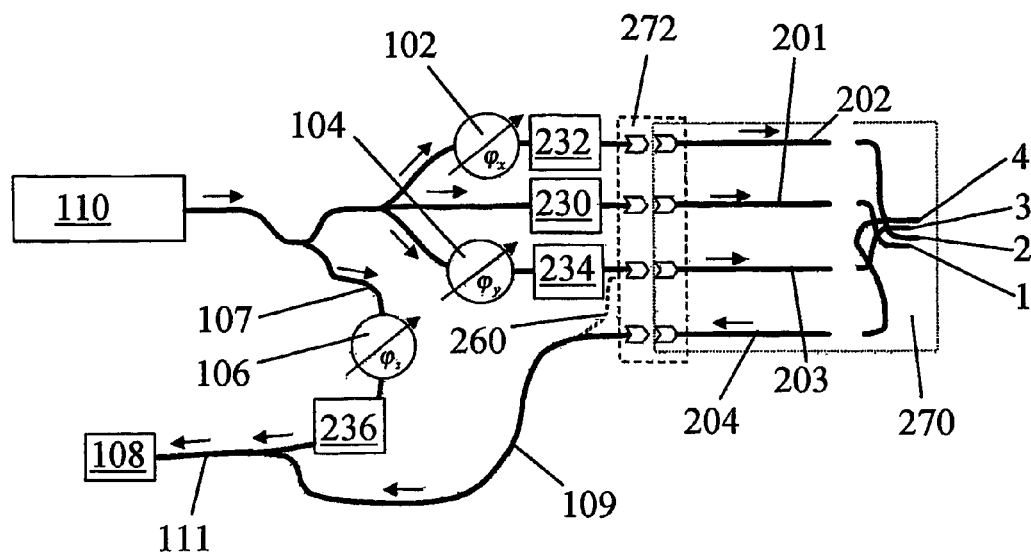
FIG. 10 is a conceptual layout of a full 3-dimensional OCT system in a preferred embodiment of the invention.

The conceptual layout of the overall 3D OCT system is shown in FIG. 10, and is based on the four-fiber configuration of FIG. 9 (although, again, a three fiber configuration is possible where at least one of the first three fibers 201, 202, 203 collects the light). Light from a wideband, low-coherence source 110 is sent into the first three fibers 201, 202, 203. Optical path lengths to the tips 1, 2, 3 of the three fibers are the same. The fourth, collection fiber 204 collects the light returning from object 122 (not shown in this illustration). The collected light is sent to a light processing system 108, which produces a signal proportional to the overall intensity of light scattered back by the object 122 and collected by fourth fiber 204 or one of the first three fibers 201, 202, 203. Each of the paths of fibers 202 and 203 comprise phase delay $\phi_y$ module 102 and phase delay $\phi_x$ module 104. Further, a phase delay $\phi_z$ module 106 is further introduced in a reference optical path 107 between source 110 and light processing system 108, and is used for conventional coherence scanning along the z axis as discussed in connection with FIG. 1. First and second fibers 201, 202 also comprise first and second modulators 230 and 232 from FIG. 6, while fiber 203 and reference optical path 107 comprise respective third and fourth modulators 234 and 236 as illustrated. Note that first fiber 201 does not need to have a phase delay module, though similarly to what was discussed in connection with FIG. 2, it may optionally comprise such a phase delay module. What is important is that there be a relative phase delay between fibers. Note also, while phase delay ($\phi_z$ module 106 and fourth modulator 236 are illustrated in reference optical path 107, that one or both of these can also be placed into an object optical path 109 carrying light between object 122 being scanned and light processing system 108. For z-scanning, object optical path 109 also joins light passing through reference optical path 107 with light striking and reflecting from the object 122 and passing through object optical path 109. In this way, the mixed optical path 111 carries a mixed reference and object signal. For z-scanning, a relative phase delay $\phi_z$ and a differential modulation is introduced as between reference optical path 107 and object optical path 109 before it light is delivered in a mixed 111 signal to light processing system 108.

In some embodiments to be discussed more fully later, the fiber tips 1, 2, 3, and (optional) 4 are assembled into a removable (and thereby disposable) probe head attachment 270, and attached via an optical connector 272 to the various elements shown to the left of optical connector 272 in FIG. 10.

In the event that one employs the three-fiber configuration of FIG. 7 and uses one of these three fibers for collection, the fourth fiber 204 is eliminated along with fourth fiber tip 4, and a three-fiber connection 260 illustrated by a dotted line in FIG. 10 is used to split the return signal out of one of the three fibers 201, 202 or 203 (203 is used in the illustration), and to feed this return signal out toward light processing system 108. In all other aspects, the conceptual layout of FIG. 10 remains the same. In either event, for z-scanning in addition to x,y scanning, there is an object optical path 109 joining light passing through reference optical path 107 with light striking and reflecting from object 122.

The fringe pattern shown in FIG. 8 is the impulse response, or instrumental function, I, 21 of the system. If the object 122 has only one, very small, scattering spot, the photo detector signal (assuming a linear detector for the moment) as a function of the spot x,y coordinate is proportional to the brightness of the fringe pattern of FIG. 8. With real scattering objects, however, having scattering areas with large numbers of scattering spots, the signal reaching the photo detector is a convolution of the object density and the instrumental function. It is apparent from FIG. 8 that the instrumental function is not localized around the center, which makes the process of deconvolution in signal processing challenging. A localized, narrow instrumental function is preferred.

This problem can be solved by shifting frequency of the optical signal in fibers 201, 202, 203, and phase detection at combinations of the frequency shifts. Some frequency shift will take place due to introduced phase delay (210, 211 in FIG. 3); the rate of change of the phase is the frequency added (or subtracted). In embodiments where the phase delay is introduced by a moving reflector similar to 116, 118, the frequency shift is the Doppler shift in the reflected light. Each optical frequency $v_{opt}$ of the signal is transformed into $v_{opt}+f_{Dopp}$, where $f_{Dopp}$ is the Doppler shift. Additional frequency shift can be introduced by amplitude or phase modulation of the optical signals. In case of amplitude modulation at a frequency f, the spectrum of each original optical frequency is transformed into three spectral components: $v_{opt}+f_{Dopp}$, $v_{opt}+f_{Dopp}+f$, and $v_{opt}+f_{Dopp}-f$.

As noted earlier, besides similarities with the phase shift produced by phase delay, the difference is that amplitude-modulated light will have spectral components that create a moving fringe pattern, but the x- (or y-) envelope of the pattern will not move (contrast FIG. 6 with FIG. 3). The phase of the "carrier" x- (or y-) fringe pattern will vary in relation to the x- (or y-) envelope with the frequency of modulation f. Delay introduced by a delay means (210 in FIG. 3), on the other hand, results in a displacement of the envelope, with the phase of the fringe pattern relative to the envelope remaining constant.

Figure 11:
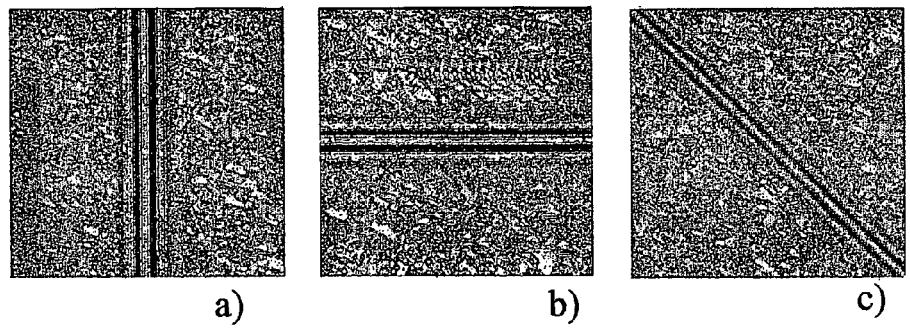
FIG. 11 is a view of low-coherence interference patterns acquired by the configuration of FIG. 10, at selected frequencies.

Light in fibers 201, 202, 203 and passing through fiber tips 1, 2, 3 is therefore modulated at different respective frequencies $f_1$, $f_2$, and $f_3$. Phase demodulation at the frequency $f_j^{Dopp}-f_k^{Dopp}+(f_j-f_k)$; (j,k=1,2,3) will result in a different instrumental function for each demodulation frequency. FIG. 11 shows the instrumental functions for each of the three detection frequencies: FIG. 11, a) for demodulation at $f_{12}=f_1^{Dopp}-f_2^{Dopp}+(f_1-f_2)$; FIG. 11, b) for $f_{13}=f_1^{Dopp}-f_3^{Dopp}+(f_1-f_3)$, and FIG. 11, c) for $f_{23}=f_2^{Dopp}-f_3^{Dopp}+(f_2-f_3)$. The maximum values (brightness of the fringe pattern) are $I_{12}=\sqrt{I_1 \cdot I_2}$, $I_{13}=\sqrt{I_1 \cdot I_3}$, and $I_{23}=\sqrt{I_2 \cdot I_3}$, respectively.

The instrumental function is still not localized around the center, which is desirable for deconvolution, as well as for envelope-only measurement. To produce the localized instrumental function, several processing options are possible.

A first option is a light processing system 108 which multiplies, rather than adds, the signals detected at $f_{12}$ and $f_{13}$. In this approach, detection of the modulated optical signal produces two electrical signals, one detected at $f_{12}$ and the other detected at $f_{13}$. Multiplication of the two electrical signals is then performed by one of the many approaches know in the art, for example, but not limited to, analog or digital multiplication. The maximum intensity in the center of the envelope is in this case $I_{12} \cdot I_{13} = I_1 \cdot \sqrt{I_2 \cdot I_3}$.

A second option is a light processing system 108 using a nonlinear photo detector, e.g., a quadratic photo detector with the output electrical signal proportional to (at least) the second power of the light intensity. While photodetectors are typically designed and optimized for high linearity, a separate broadband amplifier with nonlinear gain can easily be added to a linear detector for the desired second-harmonic detection.

Both options will produce a signal with more than one spectral component, including $v_1^+ = f_{12} + f_{13} = 2f_1 - f_2 - f_3 + 2f_1^{Dopp} - f_2^{Dopp} - f_3^{Dopp}$. Phase detection at this differential frequency produces a localized instrumental function 12, shown in FIG. 12, which is much more desirable. The central area 260, where brightness varies, is a 2D, x,y-envelope of the instrumental function. Intensity variation within the envelope is a product of the carrier fringe patterns in x and y directions (FIG. 11, a, b).

Using a third option for light processing system 108, signal at the frequency $v_1^+$ can also be produced employing digital processing of the raw signals to accomplish the same results as in the above first and second options. In this case, sampling and analog-to-digital conversion of the modulated optical signal is produced at sampling rates substantially exceeding the fastest modulation frequency, and digital processing is used to produce the signal at the differential frequency, $f_{12} - f_{13}$.

This instrumental function can be used in deconvolution as well as in envelope-only measurements. In both cases, modulation and phase shift near the light source in the optical path (FIG. 10) produces non-mechanical 3D coherence scanning of the object.

Figure 12:
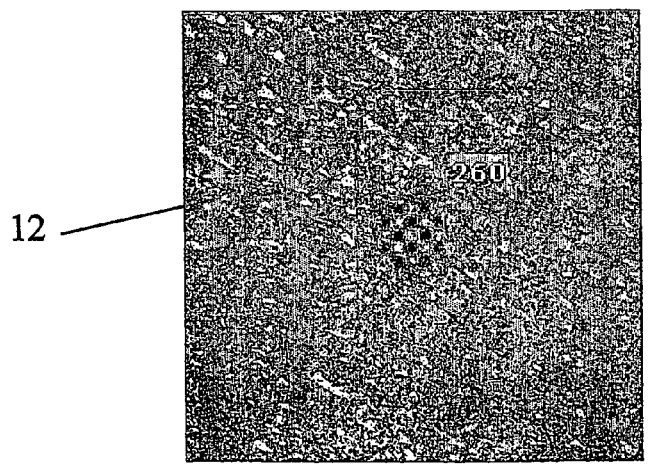
FIG. 12 is a view of the instrumental function produced by the configuration of FIG. 10, suitably localized.
Figure 24:
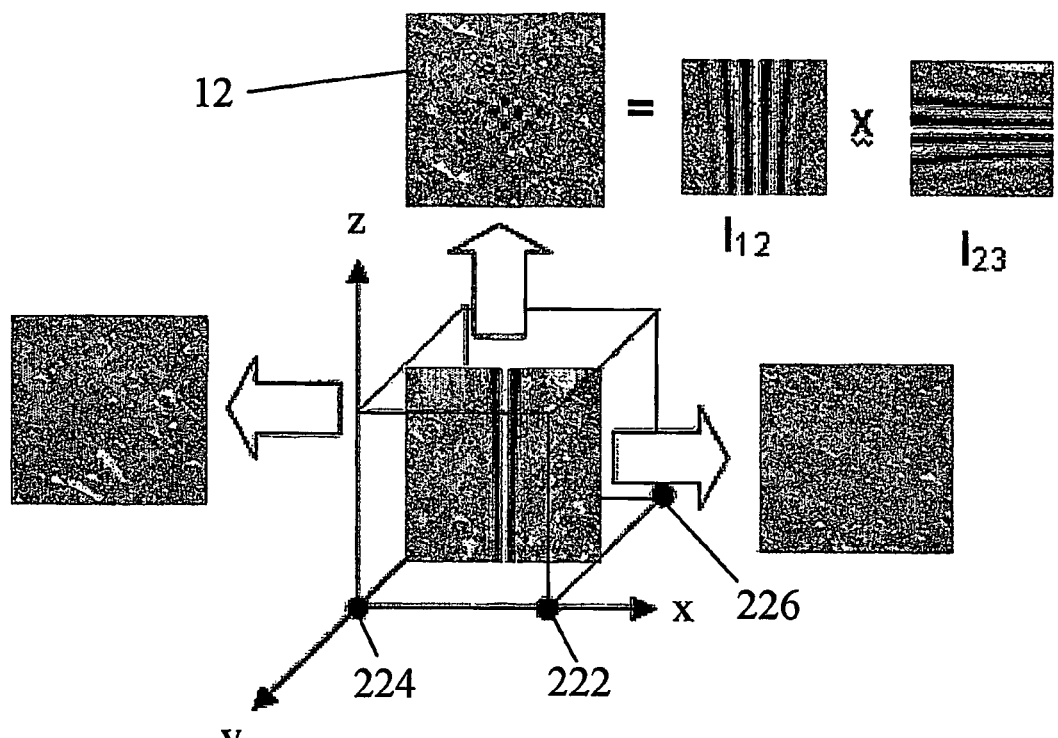
FIG. 24 illustrates the non-linear (multiplicative rather than additive) composition used to achieve the localized instrumental function of FIG. 12.

FIG. 24 illustrates the non-linear composition of the localized instrumental function 12 of FIG. 12 by light processing system 108.

Figure 13:
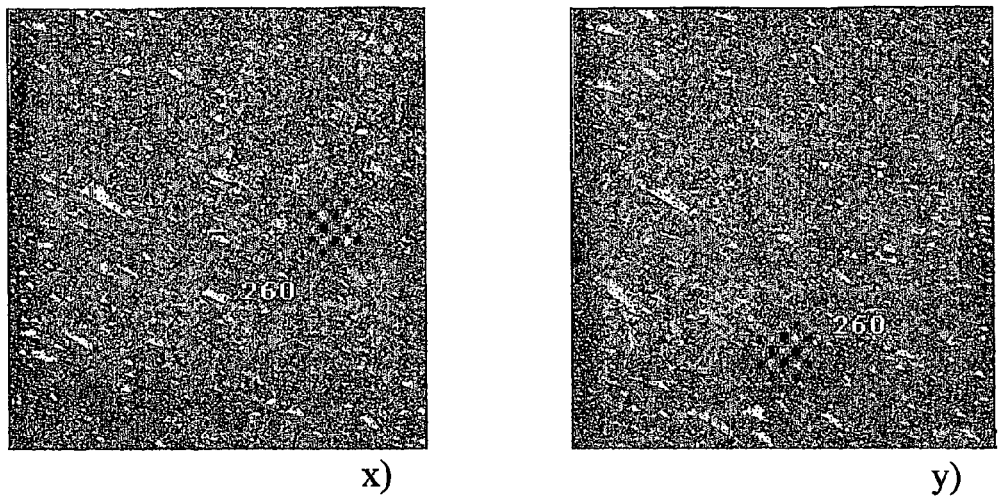
FIG. 13 shows scanning of the system instrumental function of FIG. 12 by controlled phase delay, in the x and y directions.

Referring back to FIG. 10, transverse scanning in each direction (x or y) is achieved by introducing a phase shift in one of the fibers 201, 202, 203. FIG. 13 x) shows scanning by a phase delay $\phi_x$ module 102 introduced in the optical path of fiber 202 (the fiber with tip 2 displaced along the x axis relative to tip 1). FIG. 13 y) shows scanning by a phase delay $\phi_y$ module 104 introduced in the optical path of fiber 203 (the fiber with tip 3 displaced along the y axis relative to tip 1). The introduction of these phase delays $\phi_x$ and $\phi_y$ is thus used to move the focal point of the scan of object 122 in the x and y directions, respectively. (Note again, that the 1-2 and 1-3 axes in all of these illustrations are orthogonal, but that any configuration where tips 1, 2, and 3 define a plane are acceptable.)

Figure 25:
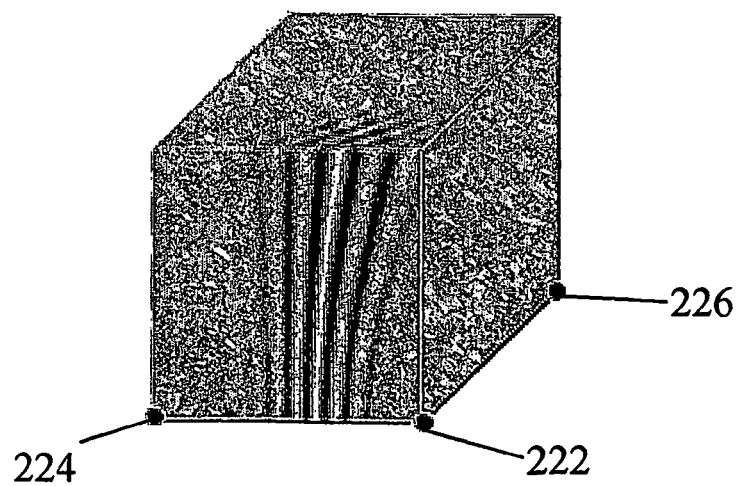
FIG. 25 shown a full three-dimensional representation of the localized instrumental functions of FIGS. 12 and 24, with a phase delay in both the x and y dimensions.

This achieves an important advance over the prior art, by replacing the need for mechanical scans in the x,y plane with fully coherence-based scanning. FIG. 25 shows a three-dimensional representation of the scan where a phase delay $\phi_x$ and a phase delay $\phi_y$ have both been introduced. The third phase delay $\phi_z$, module 106 is used to move the scan along the z axis in the conventional manner as described in connection with FIG. 1, and the instrumental function is suitably-localized.

Figure 14:
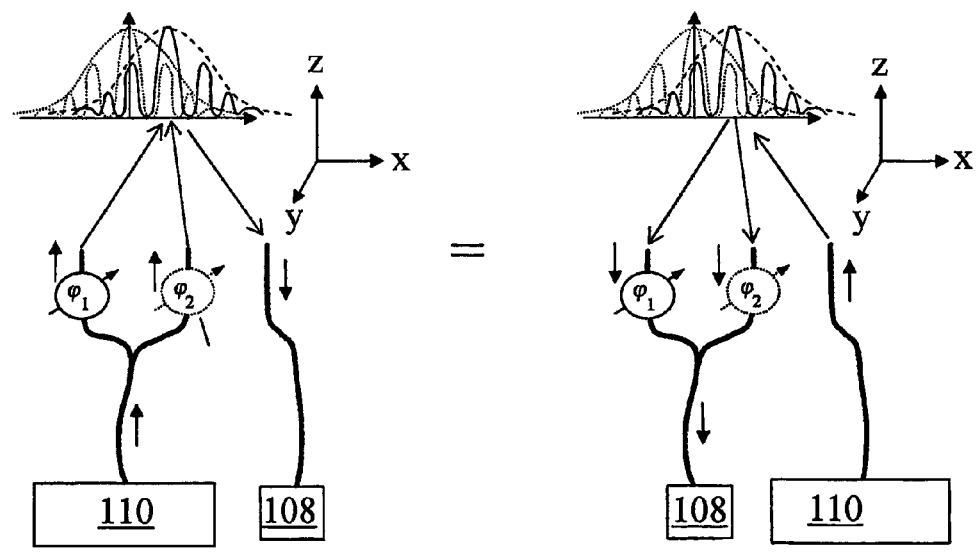
FIG. 14 schematically illustrates the interchangeability of transmitting and receiving fibers in the various OCT system embodiments disclosed herein.

It is important to observe that this system as disclosed, in all embodiment, is fully reversible. Particularly, it should be noted that the optical paths providing illumination 110 of the sample and delivering backscattered light to the light processing system 108 are interchangeable. Thus, for example, the two layouts shown in FIG. 14 are equivalent and the functionality of the OCT system is exactly the same with either of these two layouts. (Only two fibers are shown in FIG. 14 for simplicity of illustration.) One can interchange source 110 with light processing system 108 in FIG. 10, thereby reversing all of the light transmission paths, and achieve exactly the same functional result. Note also that for any individual fiber, the phase delay module and the modulators can also be interchanged; i.e., that the order in which the light passing therethrough encounters these two elements does not matter.

The above analysis describes the proposed OCT system with "phase scanning" in the x and y dimensions of the object. The required phase shift is achieved by combinations of phase delays $\phi_x$, $\phi_y$ as shown in FIG. 10. The amplitude modulations are introduced by modulators 230, 232, 234 including, but not limited to, acousto-optical modulators. An extension of the proposed method into 3D scanning of the object is achieved by introducing controlled phase shift (phase delay $\phi_z$ 106 and modulator 236 in FIG. 10—similar to the other three modulators), and processing the signals accordingly. Specifically, instead of multiplying a pair of signals as discussed earlier, groups of three signals are multiplied. Alternatively, a non-linear photo detector with cubic (third power) non-linearity can be used. And, as earlier, digital processing of the raw signals may be employed to accomplish the same results achieved by a multiplier or a cubic photo detector.

The shape of the z-envelope in the OCT signal (144, FIG. 2) is important for measurement of the z-profile of the sample. In conventional OCT, the envelope is the instrumental function of the system defining resolution of the measurement. With phase detection, the envelope is a part of the system impulse response, used for deconvolution. If coherence length is large compared to the central wavelength, the envelope is wide, and the coordinate measurement becomes ambiguous since the whole number of fringes in the measured coordinate may be miscalculated, especially in the presence of noise. Short pulses with low coherence length are used in the art for high-resolution measurements. The recent trend in OCT was to use shorter light pulses with shorter coherence length, such as Ti:$Al_2O_3$ lasers instead of super luminescent LEDs. The new light sources produce short (fs) pulses, which makes it difficult to maintain the propagating pulse shape due to dispersion in the sample and in the media preceding it in the optical path.

The alternative to short coherence lengths is a system that is capable of resolving the ambiguity of the absolute phase shift (including whole numbers of periods, or cycles) by other means. A similar problem in interferometry is solved in some cases by using light sources with more than one wavelength. In OCT, a similar approach can be implemented by using two detectors, each with a filter covering a part of the spectrum of the source. The possible proposed layout of such a dual wavelength detection embodiment is presented in FIG. 15.

Figure 1:
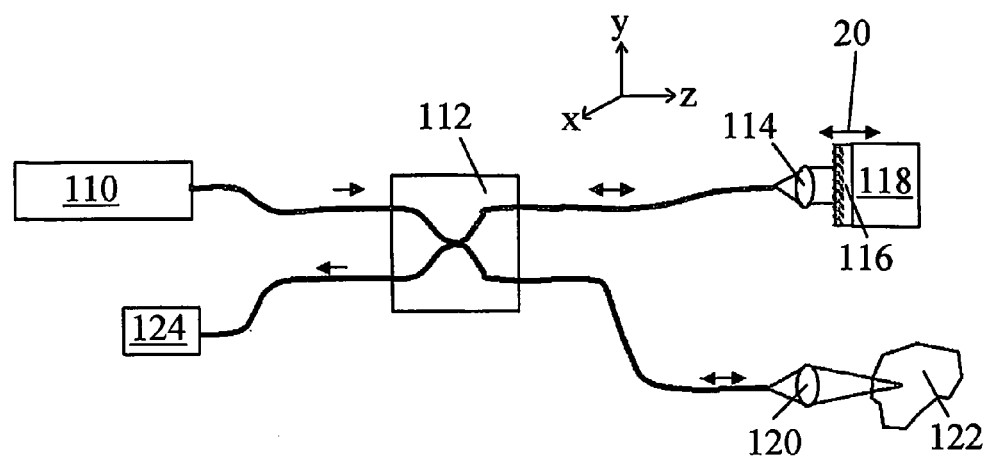
FIG. 1 schematically illustrates a typical layout of an OCT system according to prior art.
Figure 2:
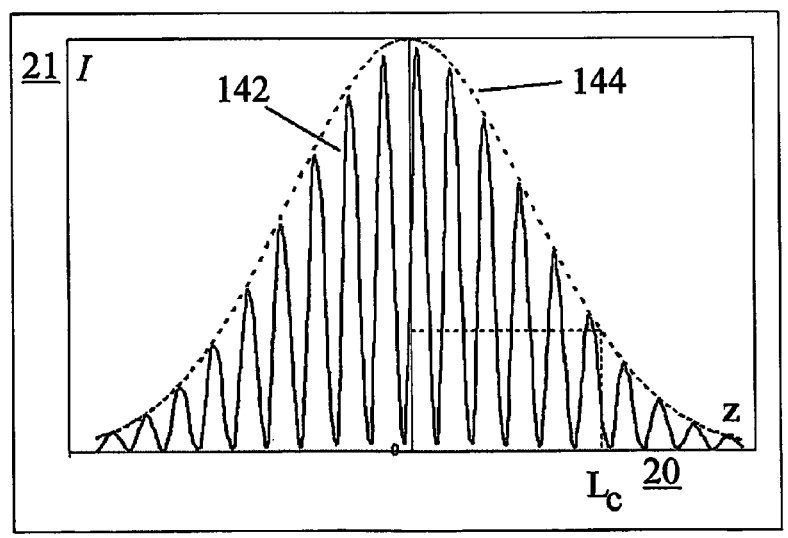
FIG. 2 is a depiction of a coherence-limited interference pattern defining impulse response of an OCT system.

Once again, this is illustrated for the x-scan only, for simplicity. The total spectral range covered by the two filters 152, 154 filtering wavelengths around different maxima (central wavelengths) and an (optional) tap 156 is the same as in conventional OCT systems such as illustrated by FIG. 1 and FIG. 2. Parallel processing of the signals of photo detectors 153 and 155 (or more generally, the light processing system 108 if a multiplier or other signal processing is employed) will therefore produce the same resolution after correlation 157, deconvolution and processing 158. The uncertainty of the number of whole periods, however, can be reduced, with the effective wavelength $$\lambda_{eff} = \frac{\lambda_1 \cdot \lambda_2}{\lambda_1 + \lambda_2}.$$

The width of each of the two components of the instrumental function, related to wavelengths $\lambda_1$, $\lambda_2$, is $$L_i^c \approx \frac{\lambda_i^2}{\Delta \lambda_i} (i = 1, 2).$$

The filter bandwidth $\Delta \lambda_i$ is yet another degree of freedom available for optimization. Both $\Delta \lambda_i$ are preferably substantially wide, comparable in bandwidth to the source, with overlapping passbands.

Signals for the two photo detectors measured simultaneously produce redundancy. This may be used to reduce the effect of noise on the measurement, which greatly benefits the success of deconvolution and resolution of the 3D profile measurement of the object. In sum, light emerging from each of the at least two filters 152, 154 is measured substantially simultaneously and correlated, thereby providing an expanded spectral range for measurement, and redundant measurement with improved signal to noise ratio.

Figure 15:
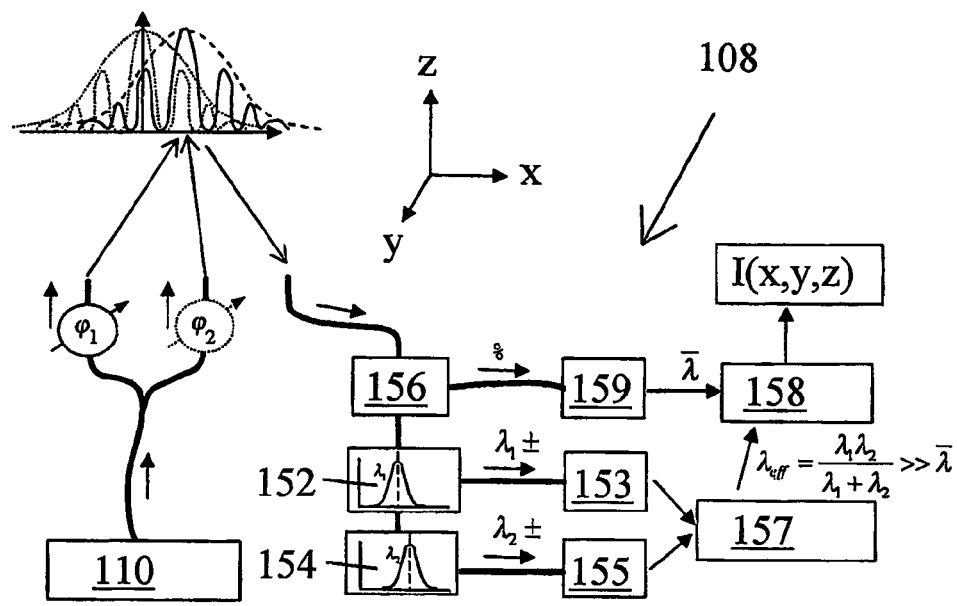
FIG. 15 schematically illustrates a dual wavelength OCT system with improved signal to noise ratio.

While two filters are shown here for illustration, more than two filters may be used, each sending a portion of the wavelength range of the backscattered light to a separate photo detector. A reference tap 156 and the photo detector 159 shown in FIG. 15 are optional, to provide an additional measurement channel, serving as a reference to reduce the effect of any possible instability in the intensity of light entering light processing system 108.

In a related embodiment (given the reversibility of the system as discussed earlier), rather than (or in addition to) multiple filters, one can employ multiple light sources. Note that FIGS. 17, 18 and 19 to be discussed below are modeled on FIG. 1 for simplicity, but can be employed in all of the embodiments disclosed herein.

Figure 17:
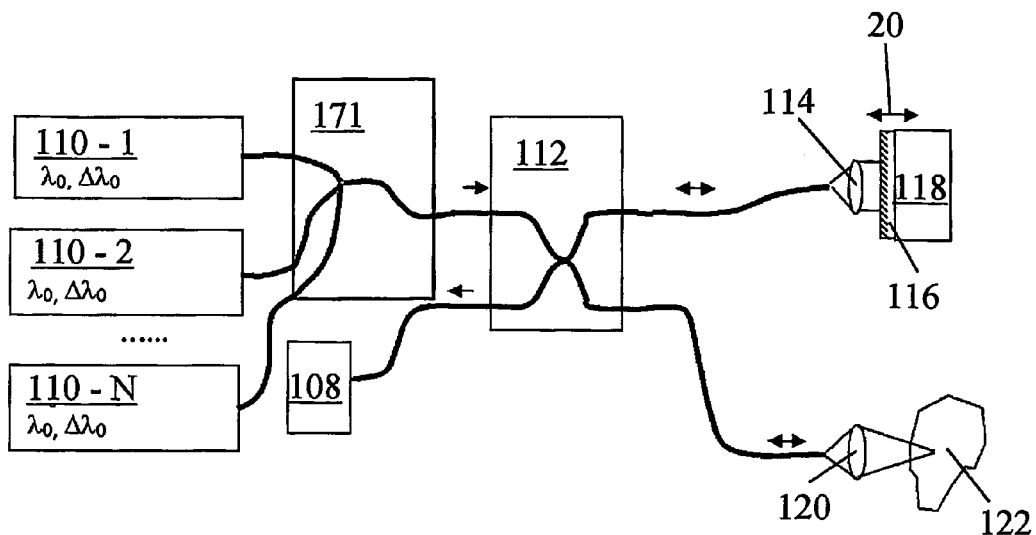

FIG. 17 illustrates an embodiment comprising more than one low-coherence light source 110-n, n=1, 2, . . . N to increase optical power and the related signal-to-noise ratio, frame rate, and other performance characteristics. Intensities of the sources are combined 171 to add incoherently, to produce one "efficient source" of the higher power equal to the power of the component sources.

Figure 18:
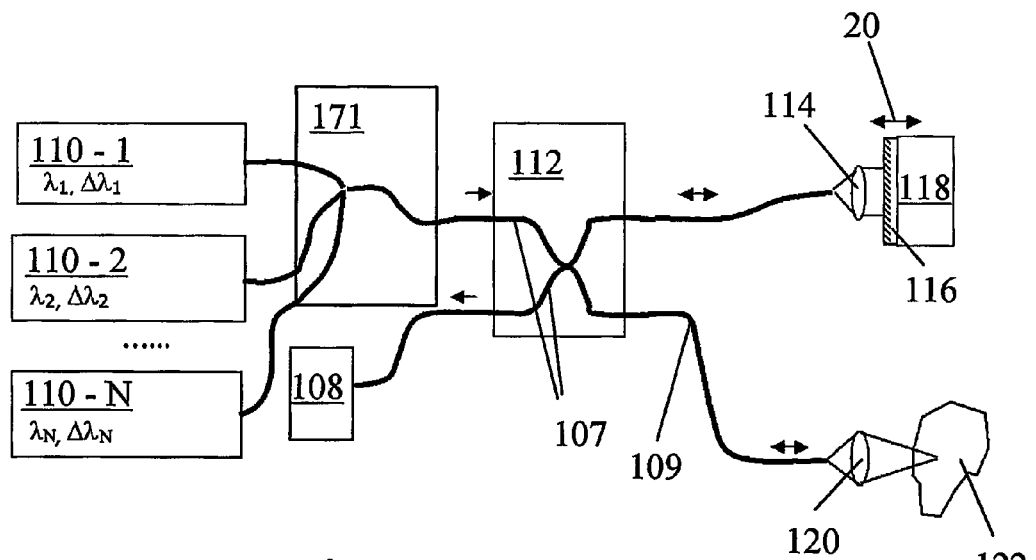
FIG. 18 schematically illustrates an embodiment comprising more than one low-coherence light source wherein the wavelengths of the sources are different.

FIG. 18 illustrates an embodiment wherein the wavelengths of the sources are different, to produce a wider overall low-coherence spectrum. In this embodiment, the interference pattern remains the same, with maximum contrast at zero path length difference between the reference optical path 107 and the object optical path 109. The coherence length, reciprocal of the spectral bandwidth, will be shorter, resulting in proportionally improved spatial resolution.

Figure 19:
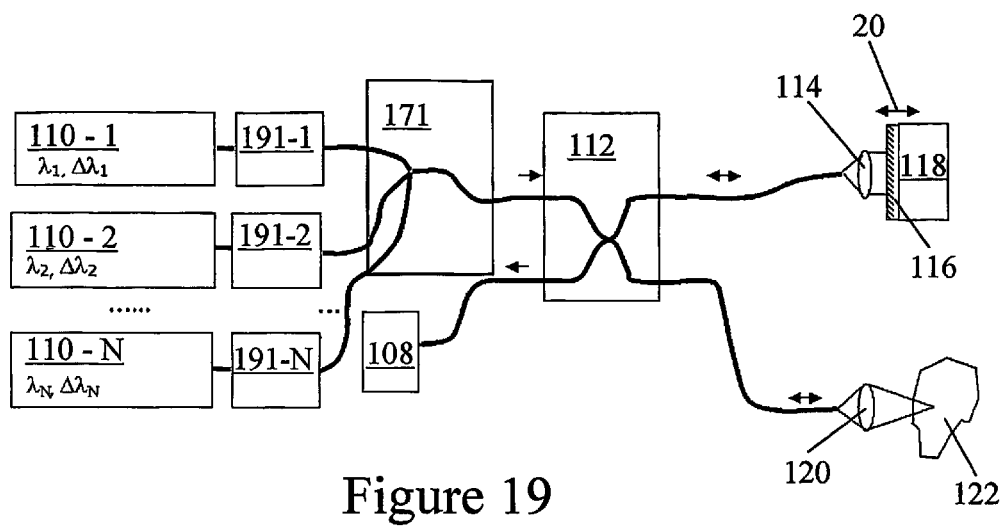
FIG. 19 schematically illustrates an embodiment similar to that of FIG. 18, wherein each source is modulated separately.
Figure 20:
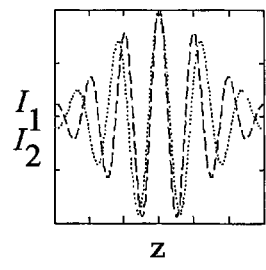
FIG. 20 is a graph illustrating two dynamic fringe patterns resulting from the embodiment of FIG. 19.
Figure 21:
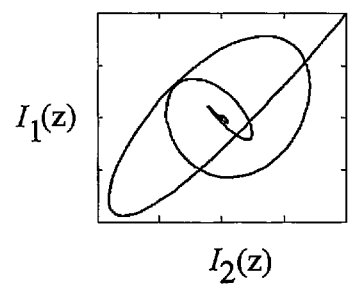
FIG. 21 is a graph illustrating phase trajectories of the fringe patterns in FIG. 20.

FIG. 19 illustrates an embodiment wherein each source is modulated separately (modulators 191-n, n=1, 2, . . . N) to provide new possibilities in signal generation and processing. For example, modulating two sources at two close, but different frequencies creates two dynamic fringe patterns is illustrated in FIG. 20. Detected synchronously, these two signals follow a phase trajectory as shown in FIG. 21, determined by the modulation frequencies and coherence lengths of the sources, which can be use for suppression of noise, e.g., by correcting the 2D vector signal to the nearest point on the phase trajectory.

Y. Zhang, M. Sato, N. Tanno, *Resolution improvement in optical coherence tomography by optimal synthesis of light-emitting diodes,* Optics Letters, Vol. 26 Issue 4 Page 205, February 2001, noted earlier, provides some pertinent discussion of multiple LED devices in free space systems.

In some alternative embodiments, the transverse (x,y) scanning of a 3D fringe pattern to produce a 3D image of the sample (object 122) can be applied to other known types of OCT where presently mechanical scanning in the x,y plane is performed. One of such types of OCT is so-called "Spectral Radar"—an OCT sensor working in the Fourier domain (see, e.g., G. Hausler, M. W. Linder, *"Coherence radar" and "spectra; radar"—new tools for dermatological diagnosis,* J. Biomd. Opt. 3(1)21-31, 1998, and P. Andretzky, M. W. Linder, J. M. Hermann, A. Schultz, M. Konzog, F. Kiesewetter, G. Hauser, *Optical coherence tomography by spectral radar: dynamic range estimation and in vivo measurements of skin,* Proc. SPIE 3567, 78-87, 1998. Similar to the above, using at least three fibers for illumination and collection of light, to produce a 3D fringe pattern, combined with amplitude modulation and phase detection, will allow retrieving the 3D object profile instead of depth (z) profile measurement alone.

The disclosure herein can also be applied in optical coherence microscopy (OCM). In OCM, unlike OCT, the sample may be opaque. The 3D information about the surface scattering of the sample and therefore the 3D surface shape is characterized in OCM, whereas in OCT the 3D structure of the sample volume is imaged.

Optionally, more than two fibers for each transverse scan direction (more than three total) can also be used, e.g., to improve the shape of the instrumental function of the apparatus. In particular, the effects of improved instrumental function and higher resolution may be provided by the operation of the multiple fiber sources as a optical phased array (OPA), as known in the art.

Depending on the size of the object and the distance to it, different modifications of the fiber tips 1, 2, 3 may be employed for object illumination at different distances. With no modification, the illuminated area of object 122 has the size 2NA·h, where NA is the fiber numerical aperture and h (see FIG. 3) is the distance to the object. If larger areas or shorter distances are desired, beam expansion will be achieved by expanding the beam using, for example, not limitation, lenses (spherical, aspheric, or gradient-index), tapered fibers, or similar or equivalent devices known or which may become known in the at.

When the distance h to the object is comparable or small compared to distance d between the fiber tips (see FIG. 3), beam deflectors may be used to change the direction of light exiting from the fibers, so that the centers of the two light spots are both approximately coincident with the center of the object. Such deflectors may include, but are not limited to, prism attachments, fiber end polishing (or other preparation) at an angle, bending of the fibers, and reflecting surfaces. A common lens may also be used for all fibers, similar to dual- and multiple-fiber fiberoptic collimators.

Resolution of the OCT system depends on distance h to the object. When this distance is small compared to distance d between the fiber tips, the period of the fringe pattern (FIG. 3) is equal to half the wavelength. With signal processing and deconvolution, this may be an approximate value of the system resolution. For envelope-only measurement, resolution is worse, but still proportional to the fringe period, since a fixed number of fringes are contained in the envelope. Resolution is compromised as the distance to the object increases. Resolution can be improved by increasing the distance d between the fiber tips.

Figure 16:
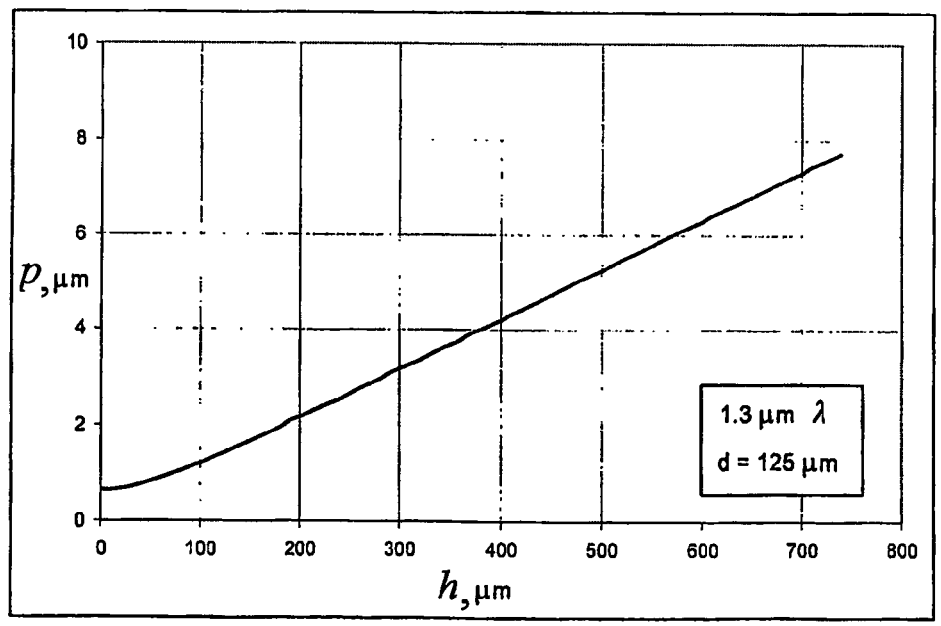
FIG. 16 is a plot of a fringe width as a function of distance to the object.

FIG. 16 shows calculated period of the fringe pattern p as function of h, for the 1.3 micron wavelength and d=125 microns. These resolution estimates are for transverse (x,y) resolution. Resolution in depth (z) is the same as in conventional OCT systems described in the prior art.

Returning to FIG. 10, it is again noted that the fiber tips are assembled into a removable (and thereby disposable) probe head attachment 270, and attached via an optical connector 272 to the various elements shown to the left of optical connector 272 in FIG. 10. In this way, this new design provides for low-cost, disposable probe tips. The probe needs no rotation or other mechanical motion, unlike existing OCT systems. The probe is also flexible. Its cross-section can be very small, e.g., 0.25 by 0.25 mm if standard single-mode fiber (SMF) with 125 µm cladding diameter is used. This translates into a 0.0625 mm$^2$ cross-section, small enough for installing in needles and close to the cross-section of a standard 0.014" guidewire such as used in vascular diagnostic and interventional procedures. Since the core diameter of the standard SMF is only ~19 µm, the 125 µm cladding diameter can be reduced even more, e.g., by chemical etching, to further minimize the probe size.

Figure 26:
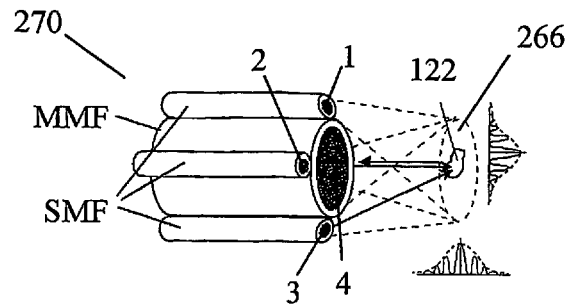
FIG. 26 illustrates a first embodiment of a probe head design for use in accordance with various embodiment of the invention.

A detailed view and operation of an embodiment of fiber probe tip 270 suitable for use in accordance with various embodiment of the invention is shown in FIG. 26. The sample (object) 122 is illuminated by diverging light emitted by fiber tips 1, 2, and 3, which are beveled, deflecting the diverging beams and forming the 3D interference pattern substantially overlapping over a full field of view 266 at an intended distance of object 122 to be scanned from fiber tips 1, 2 and 3, as has been disclosed herein. Note that the light beams are unfocused when they strike object 266. Backscattered light (in a four-fiber system) is collected by the fourth fiber tip 4. (Recall that everything can also be reversed, see FIG. 14) Each element of resolution ("3D pixel") in the sample (object 122) contributes to the backscattered optical signal with an amplitude defined by its reflectivity (scattering) on the one hand, and a phase defined by its location in relation to the illuminating fibers, on the other hand. The 3D sample image is reconstructed from the detected signal by nonlinear light processing system 108 as discussed previously. Another possible implementation, as discussed earlier, is to use one (or more) of the fiber tips 1, 2, or 3 for collection of backscattered light, eliminating the for the fourth fiber tip 4.

Referring to FIG. 26 (and FIG. 27 to be discussed below), it should be noted that while illuminating 40 fibers 201, 202, 203 may preferably be chosen single mode, the collection fiber 204 may preferably be multimode, thus providing higher light collection efficiency due to larger core diameter and higher numerical aperture.

Figure 27:
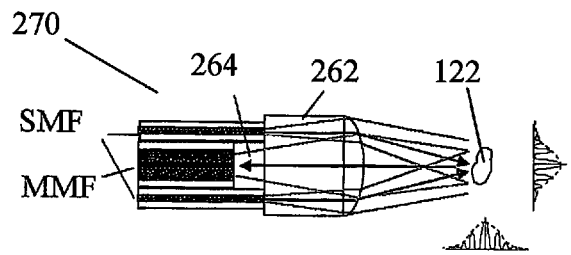
FIG. 27 illustrates a second embodiment of a probe head design for use in accordance with various embodiment of the invention.

An alternative embodiment of fiber probe tip 270 is shown in FIG. 27. The third single-mode fiber, displaced from the plane of the drawing, is present, similar to FIG. 26, but hidden in the view presented. A probe head tip refractory element 262 changes the divergence and direction of the illuminating beams emerging from the single-mode fibers, and also improves collection of the backscattered light into the multimode receiver fiber. FIG. 27 illustrates refractory element 262 inwardly refracting the diverging light from each fiber. While refractory element 262 in some circumstances may converge the light emerging from fiber tips 1, 2, and 3, it is important in all cases that this light substantially overlap over the full field of view 266 at an intended distance of object 122 to be scanned from fiber tips 1, 2, and 3, and that it not be focused at a single spot, i.e., pixel of sample 122. A length of an optional pellet 264 is selected to adjust the optimal distance to the tip of the receiver fiber, preserving the monolithic structure with no air gaps. All components are connected by standard means employed in fiber optics, such as thermal splicing or adhesion. The lens focal length, its length, and the distance to the fibers provide several degrees of freedom for controlling illumination of the sample (angle between beams and related period of interference pattern) and collection of backscattered light. It is important to note again that the imaging remains unfocused, similar to the layout of FIG. 26. The depth of field limitation, typical of conventional OCT which requires focusing, is thereby not a factor. The high resolution and image details in all three dimensions result instead from digital processing of the photodetector signals.

It should be noted again that the optical paths providing illumination of the sample (object) 122 and the path delivering backscattered light to the photodetector are interchangeable, as discussed in connection with FIG. 14. When the system is reversed, fourth fiber tip 4 serves as the sole source of illumination of the sample (object) 122, and fiber tips 1, 2, and 3 collect backscattered light to produce interference on the surface of the photodetector, similar to conventional OCT. "Effective interference pattern" is created in the sample (object) 122 in both conventional OCT and the OCT devices and method disclosed herein. The difference is that the devices and methods disclosed herein produce a 3D scan with localized instrumental function and without physical movement, as opposed to 1D coherence scanning of conventional OCT.

The amount of light on the photodetector in the 3D OCT disclosed herein with focus-free imaging may be lower, compared to standard OCT with a lens that focuses light in the sample (object) 122. However, with the smaller volumes under examination typical of cellular imaging, the amount of light is quite sufficient A radiometry calculation performed in preliminary studies is described below related to signal deconvolution.

Resolution of the proposed OCT devices and method disclosed herein depends on the distance to the object. As the distance to the point-in-sample increases, imaging resolution will deteriorate, for two main reasons: decreasing signal-to-noise ratio and increasing fringe width. The effect of signal-to-noise ratio is discussed in detail below. The fringe width increases with the distance h as $0.5\lambda\sqrt{1+(h/2d)^2}$, where $\lambda$ is the central wavelength and d is the distance between illuminating fiber tips. For values typical of cellular imaging, h is comparable to d, and expansion of the fringes is not dramatic. Resolution can be improved by increasing the distance d between the fiber tips of the probe. The tradeoff between resolution and probe is one of the parameters optimized in system design.

Image acquisition rate is limited by the electronics and processing only, which is superior to the present OCT systems which largely rely on mechanical scanning of the focal spot. By maximizing the acquisition rate, real-time video rates at 30 frames per second should be feasible. Coherence scanning in all three dimensions of the proposed 3D OCT, unavailable to the existing OCT technologies, will enable a breakthrough improvement in acquisition speed.

The disclosure is also applicable to elimination of mechanical scanning in X and Y dimensions in existing OCT systems with no scanning in the depth dimension, such as "spectral radar." (P. Andretzky, M. W. Lindner, W. Michael, J. M. Herrmann, A. Schultz, M. Konzog, M. F. Kiesewetter, G. Hausler, *Optical coherence tomography by spectral radar:*

*dynamic range estimation and in-vivo measurements of skin,* Proc. SPIE 3567, p. 78-87, 1999. Image acquisition speed of the disclosed system should exceed that of the present state of the art by at least an order of magnitude due to phase scanning replacing the conventional mechanical X,Y scanning.

Deconvolution in OCT, described in the literature, produced limited improvement in the image resolution, due to noise. A factor of 2.5 increase in "image sharpness" was obtained at a loss of dynamic range of 2 dB using iterative restoration algorithm. (A. M. Rollins, M. D. Kulkarni, S. Yazdanfar, R. Ungarunyawee, J. A. Izatt, *In vivo video rate optical coherence tomography,* Optics Express, Vol. 3, No. 6, pp. 219-229, 1998; and M. D. Kulkarni, C. W. Thomas, J. A. Izatt, *Image enhancement in optical coherence tomography using deconvolution,* Electronics Letters, vol. 33, No. 16, pp. 1365-1367, 1997.) The recent progress in ultra low noise photodetectors, driven largely by fiberoptic telecommunications applications, is promising to enable more efficient deconvolution in OCT. In addition, the approach to cellular imaging with deconvolution disclosed herein differs from attempts described in the literature by reducing the field of view and depth of imaging, which is justified by the gain in resolution, reaching the micron length scale.

An important limitation of conventional OCT systems is due to the use of a focusing lens. In such conventional systems, certain lens design issues, such as aberrations affecting focusing and coupling of backscattered light into receiver fiber, typically define practical distances between the probe and the sample in the millimeter range. As a result, the signal-to-noise ratios (SNR) are typically relatively low. This compromises the efficiency of image deconvolution, as was just discussed.

Figure 28:
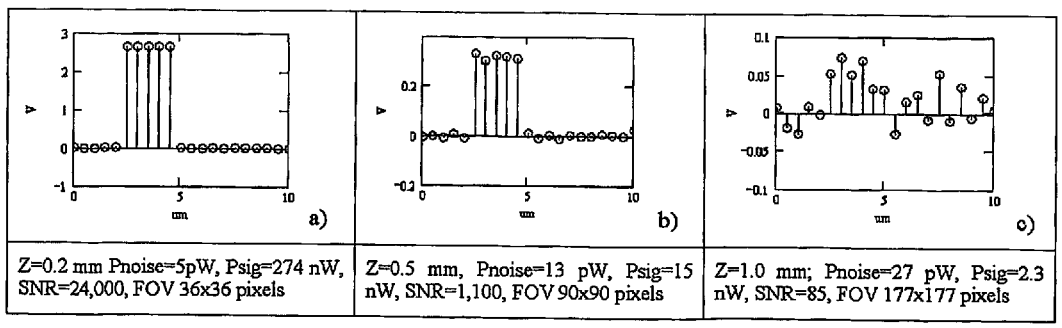
FIG. 28 illustrates some modeling results of the OCT devices and methods disclosed herein, with deconvolution.

In the present invention, light in the sample is not focused, and due to the sample illumination over the over a full field of view 266 (see FIG. 26) rather than on a single focal spot, and processing of backscattered light with an unfocused, 3D fringe pattern, closer distances are possible between the probe and the sample. As a result, higher SNR becomes possible, enabling efficient image deconvolution. This ultimately results in higher resolution, potentially at the micron and submicron levels, as illustrated in the modeling results presented in FIG. 28 as discussed below. This capability is of particular value for cellular imaging and inspection of microscopic structures FIG. 28 presents preliminary modeling suggesting that micron-level resolution is likely to be feasible, to enable cellular imaging in 3D OCT. The calculations assumed an SLD light source with the 1300 nm wavelength, 40 nm spectral bandwidth (coherence length Lc=42 μm), and 30 mW optical power. Numerical aperture of the single-mode fibers is 0.1, diameter of the receiver fiber 100 μm, object feature is square 5 μm on the side, resolved to 1 μm; reference optical power is 30 μW. The photodetector was assumed Analog Modules 712A-4, with sensitivity 77 V/μW and noise 20 fw/Hz$^{1/2}$. Refractive index of different element of cells varies from 1.38 in rat liver cells (J. Beuthan, O. Minet, J. Helfman, G. Muller, *The spatial variation of the refractive index in biological cells,* Physics in Medicine and Biology, vol. 41, pp. 369-382, 1996) to 1.7 in melanin. (I. Vitkin, J. Woolsey, B. Wilson, and R. Anderson, *Optical and thermal characterization of natural (sepia oficinalis) melanin,* Photochemistry and Photobiology, vol. 59, pp. 455-462, 1994.) The calculation assumed Δn=0.05 between the feature being imaged and the background, resulting in intensity reflection of approximately 0.1%; frame rate 30 FPS, scattering in the tissue 1 mm$^{-1}$ (S. J. Matcher, M. Cope, D. T. Delpy, *In vivo measurements of the wavelength dependence of tissue-scattering coefficients between 760 and 900 nm measured with time-resolved spectroscopy* Applied Optics, Vol. 36, No. 1, pp. 386-396, 1997), the distance to the feature inside the sample varied between 0.2 and 1 mm. The target resolution was 1 μm, which defined the amount of optical power from a "pixel" and the signal to noise ratio. The detected signal intensity was calculated accounting for losses due to geometry, scattering, modulation, and polarization effects.

Retroreflection by the object (0.1%) was assumed to be a step function 5 μm wide, sampled at the 1 μm resolution; the OCT impulse response (or point spread function, PSF) was sampled similarly. Convolution of the reflection and PSF was produced by multiplying their Fast Fourier transforms (FFT). Next, bandwidth-limited noise was added to the convolution. Detection bandwidth was selected equal to the Nyquist frequency. Next, deconvolution of the noisy signal was performed by dividing the Fourier transform of the noisy OCT signal by the Fourier transform of the PSF and applying the inverse FFT. The results for thee sample distances are presented in FIG. 28.

At a distance of 0.5 mm, imaging cells with 1 μm resolution and small effect of noise appears possible. The resolution increase due to proper filtering and deconvolution is encouraging, considering the assumed coherence length $L_c$=42 μm. The 3D field of view of 90×90×90 results in nearly megapixel 3D image sizes in each frame; with the assumed frame rate of 30 FPS, the video stream will be approximately 30 MB per second. Also shown is the modeling for 0.2 mm, which shows an even smaller noise effect. At a distance of 1 mm, the SNR value of 85 is not sufficient for effective deconvolution, and the noise effect is detrimental.

The above results illustrate a mathematical model available for designing the 3D OCT setup. The model can be employed for selection of components with a clear understanding of their effect on the overall system performance. Requirements to components may be specified using the model. The effect of wavelength, spectral range, and power of the SLD can be immediately estimated. Tradeoffs between performance characteristics such as depth range, frame rate, resolution (feature size and number of pixels), and others can be selected using the model.

Several other technical considerations are also recognized, as follows:

Speckle effects are known to be a problem in standard OCT. Speckles appear when unresolved features of an object scatter coherent light with significant mutual phase shifts. The phase shifts vary as the observation angel changes, resulting in apparently random intensity modulation of the image. In the high-resolution 3D OCT proposed herein, the resolved feature size will be comparable to the wavelength. Therefore, the effect of speckles can be expected to be small.

Regarding fiber dispersion, for efficient light collection and improved signal-to-noise, the receiver fiber (204 in the four-fiber embodiments) preferably is multimode, with the core diameter larger than in single-mode fibers. Modal dispersion, or differential mode delay (DMD) is the result of different rays of light traveling over different pathways within the fiber core. Since each pathway has a different length, the time of arrival of each ray is a function of the distance traveled. DMD in multimode fibers is typically on the order of 1 ps/m (J. E. George, S. Golowich, P. F. Kolesar, A. J. Ritger, and M. Yang, *Laser Optimized Multimode Fibers for Short Reach 10 Gbps Systems,* National Fiber Optic Engineers Conference, 2001 Technical Proceedings, pp. 351-361). Modulation frequencies in 3D OCT should not exceed 100 MHz. Typical length on the fiber is ~1 m. The resulting conservative estimate of the DMD-related phase shift in our case is therefore $10^{-4}$. This amount is small compared to $2\pi$, and the effect of DMD on the system performance should be negligible.

It is expected that other dispersion effects, such as polarization mode dispersion (PMD) in the fiber stretcher, will be negligible as well due to relatively low (tens of MHz at most) modulation rates.

Note that while at least three fibers are required for 3-dimensional OCT scanning, the disclosure herein can also be applied to 2-dimensional scanning, in the x-z or x-y planes. This is useful for situations in which a two-dimensional scan is all that is required, for example, in scanning thin films, or in taking two-dimensional cross-sectional scans of a three-dimensional object where motion is supplied along the third dimension, such as a material being extruded.

All-fiber imaging as disclosed herein with dramatically reduced cross-section will enable the first "camera through a needle". The reduced size and weight of the 3D OCT and flexible probe with low cross-section will allow for in-vivo histological imaging of tissues and cells, in a minimally invasive procedure. Focus-invariant registration of low-coherence interference patterns will provide extended depth of field unavailable with present OCT.

The technical issues of existing OCT result in a reduced scope of its commercial applications, currently limited to ophthalmology. The 3D OCT disclosed here with simple, passive, flexible, low-cost, and disposable probes will enable practical applications for functional biological imagery (three-dimensional imagery of the sample on a cellular scale) and commercial applications, including clinical biomedical imaging for diagnostics of cancer and pre-cancer and cardiovascular diagnostic imaging.

Acquisition and processing at video frame rates will enable real-time 3D OCT imaging and storage of large numbers of cross-sectional views of living cells. This will enable real-time monitoring of cell dynamics in biological and biophysical experiments. In medical applications, the 3D OCT combined with optional spectroscopic imaging will provide real-time "virtual biopsy" to be presented to the user with head-mounted stereoscopic display or in traditional multiple cross-sectional views as in CT-scan.

Resolution of existing OCT systems employs "envelope only" measurement with the resolution defined by the coherence length of the source, typically on the order of 10 microns. Due to noise, prior attempts to apply deconvolution to OCT signals did not result in dramatic resolution enhancement The proposed development of high-resolution 3 OCT, fully applicable to cellular imaging, will now be based on a novel probe geometry and leveraged by the recent progress in low-noise optoelectronics and new commercially available components.

This disclosure can help to create probes using diffused light-scattering principles that can monitor the eye, skin, and brain health of living beings. This can aid research work centered on the eventual design of a goggle-like device that combines the dynamic light scattering probe with other techniques including corneal autofluorescence, laser Doppler velocimetry, reflectometry and oximetry, optical coherence tomography, and laser scanning technology (http://www-.medicaldesignnews.com/full_story.php?WID=652). This technology will also serve as a tool of functional imagery with enhanced capability to image functioning biological systems at the cellular length scale, with three-dimensional imagery of the sample. Finally, 3D OCT will be applicable for diagnostics of the performance of labs-on-a-chip, including detecting the presence of bubbles and particles and removing or characterizing them, as well as measurement of fluidic movement.

Biomedical imaging for diagnostics and minimally invasive surgery is a significant application. The market of diagnostic biomedical imaging grows at a steady rate of over 10 percent annually and is expected to reach $20 Billion in 2007. OCT offers resolution of imaging by at least order of magnitude better than ultrasound, X-Rays, CAT scan, or MRI. Traditional OCT has found very limited commercial applications, largely due to the mechanical motion in the probe. Known commercial OCT system, produced by Zeiss-Humphrey Systems, appear to be limited to diagnostics of the eye retina. It appears that no commercial OCT tools for other parts of the body currently exist, leaving over 90 percent of the potential commercial applications unaddressed. With the flexible, low-cost, disposable probes, the disclosed 3D OCT will enable the first OCT tool for commercial application in medicine, beyond ophthalmology. The probe cross-section compatible with standard guide wire will enable applications in cardiovascular diagnostic imaging. In oncology, Pap Smear test alone is nearly a billion dollar market. The "3D OCT camera through a needle" with optional spectroscopic capability will produce "biopsy movies" to be presented to a radiologist in the familiar microscopic format, as well as an optional "visual reality" real-time imaging with a head-mounted display. In minimally invasive surgery, the 3D OCT can work in combination with conventional endoscopes to provide "close-up" three-dimensional views of cells in the areas of interest. Fiber probes can also be attached to surgical instruments (e.g., scissors or lancets) for imaging of tissues and cells ("real-time biopsy") during surgery.

Other potential biomedical applications are in ophthalmology; developmental biology; dermatology; dentistry; gynecology; urology; gastroenterology; laryngology; surgical guidance and intervention. Non-biomedical applications of 3D OCT are envisioned in high-density data storage, polymer matrix composites, inspection systems for semiconductor and MEMS manufacturing, and industrial inspection systems.

Another application is real time 3D imaging of plant cells. A plant cell is much more mobile than an animal cell. Movement within a cell may be deep within tissue.

Microgravity effect on the immune system are also of interest. For example, extended duration spaceflight produces reduced immune response, possibly through alteration of basic cellular functions. Results indicate that by day four of a spaceflight mission, the cell-mediated immune system is noticeably degraded. Changes in cell shape are not monitored at the early stages, so it is unknown when such changes take place. Research in cellular biology, particularly in the area of cells that experience microgravity, indicate that changes in cells that adapt to microgravity could be initiated by physical changes that occur in the first few seconds/minutes of that environment. Furthermore, increased sensitivity to bacterial allergens is a particular problem. Studies have not revealed whether this is due to stress or microgravity. The proposed development will permit the studies of the effects of microgravity on cell samples in the earliest stages of exposure to microgravity, providing information for fundamental space biology and bioastronautics.

3D OCT can also be applied for examining biological structures in biochips. Plastic molded biochips show great promise as high-throughput screening and point-of-care biosensing technologies. Today these on-chip chemical and biochemical analysis schemes are limited by the availability of highly sensitive detection methodologies. 3D OCT with several multiplexed probes will enable speedy and robust examination of biochips. In addition, Doppler velocimetry, available in 3D OCT as well as in traditional OCT, will provide high-resolution noninvasive velocity determinations. 3D OCT will facilitate detection in volumes ranging from 10s of microliters to 10s of picoliters, thus reducing sample volume requirements and enabling a broad range of materials to be analyzed.

Other applications requiring real-time 3D imaging of living cells will be accommodated by the proposed technology as well.

While only certain preferred features of the invention have been illustrated and described, many modifications, changes and substitutions will occur to those skilled in the art It is, therefore, to be understood that the appended claims are intended to cover all such modifications and changes as fall within the true spirit of the invention.

I claim:

1. An optical coherence tomography apparatus, comprising:
   a first optical fiber (201), comprising a first fiber tip (1) thereof;
   a second optical fiber (202), comprising a second fiber tip (2) thereof displaced from said first fiber tip (1) substantially in a fiber tip plane (71) substantially normal to an optical axis (72) of said apparatus; and
   a phase delay $\phi_x$ module (102) introducing a relative phase delay between said first optical fiber (201) and said second optical fiber (202); wherein:
   adjustment of said phase delay $\phi_x$ module (102) enables scanning of an object (122) in a one-dimensional direction parallel to the displacement between said first fiber tip (1) and said second fiber tip (2) and
   not counting any collection fibers (204), said apparatus consists of no more optical fibers than said two optical fibers for said scanning in said direction parallel to said displacement between said first fiber tip (1) and said second fiber tip (2).

2. The apparatus of claim 1, further comprising:
   a third optical fiber (203), comprising a third fiber tip (3) thereof displaced from said first fiber tip (1) and said second fiber tip (2) substantially in said fiber tip plane (71), such that said first fiber tip (1), second fiber tip (2) and third fiber tip (3) define said fiber tip plane (71); and
   a phase delay $\phi_y$ module (104) introducing a relative phase delay between said first optical fiber (201) and said third optical fiber (203); wherein:
   adjustment of said phase delay $\phi_y$ module (104) enables scanning of the object (122) in a direction parallel to the displacement between said first fiber tip (1) and said third fiber tip (3); and
   not counting any collection fibers (204), said apparatus consists of no more optical fibers than said three optical fibers for said scanning through a 2-dimensional plane parallel to said fiber tip plane (71); whereby:
   said adjustment of said phase delay $\phi_x$ module (102) in combination with said adjustment of said phase delay $\phi_y$ module (104) enables scanning of the object (122) through said 2-dimensional plane parallel to said fiber tip plane (71).

3. The apparatus of claim 1, further comprising:
   a phase delay $\phi_z$ module (106) for introducing a relative phase delay between a reference optical path (107) and an object optical path (109) of said apparatus; wherein:
   adjustment of said phase delay $\phi_z$ module (106) enables scanning of the object (122) in a direction substantially parallel to the optical axis (72); whereby:
   said adjustment of said phase delay $\phi_x$ module (102) in combination with said adjustment of said phase delay $\phi_z$ module (106) enables scanning of the object (122) through a 2-dimensional plane defined by the displacement between said first fiber tip (1) and said second fiber tip (2), and the optical axis (72).

4. The apparatus of claim 2, further comprising:
   a phase delay $\phi_z$ module (106) for introducing a relative phase delay between a reference optical path (107) and an object optical path (109) of said apparatus; wherein:
   adjustment of said phase delay $\phi_z$ module (106) enables scanning of the object (122) in a direction substantially parallel to the optical axis (72); whereby:
   said adjustment of said phase delay $\phi_x$ module (102) in combination with said adjustment of said phase delay $\phi_y$ module (104) in further combination with said adjustment of said phase delay $\phi_z$ module (106) enables scanning of the object (122) through a 3-dimensional volume.

5. The apparatus of claim 2, further comprising:
   a first modulator (230) for modulation of light passed through said first optical fiber (201);
   a second modulator (232) for modulation of light passed through said second optical fiber (202);
   a third modulator (234) for modulation of light passed through said third optical fiber further (203); and
   a non-linear light processing system (108) of at least of second power with respect to an intensity of light passed through said first modulator (230), said second modulator (232), and said third modulator (234), thereby producing a localized, 2-dimensional instrumental function.

6. The apparatus of claim 3, further comprising:
   a first modulator (230) for modulation of light passed through said first optical fiber (201);
   a second modulator (232) for modulation of light passed through said second optical fiber (202);
   a fourth modulator (236) for modulation of light passed through said reference optical path (107); and
   a non-linear light processing system of at least of second power with respect to an intensity of light passed through said first modulator (230), said second modulator (232), and said fourth modulator (236), thereby producing a localized, 2-dimensional instrumental function.

7. The apparatus of claim 4, further comprising:
   a first modulator (230) for modulation of light passed through said first optical fiber (201);
   a second modulator (232) for modulation of light passed through said second optical fiber (202);
   a third modulator (234) for modulation of light passed through said third optical fiber further (203);
   a fourth modulator (236) for modulation of light passed through said reference optical path (107); and
   a non-linear light processing system (108) of at least of third power with respect to an intensity of light passed through said first modulator (230), said second modulator (232), and said third modulator (234), and said fourth modulator (236), thereby producing a localized, 3-dimensional instrumental function.

8. The apparatus of claim 2, wherein:
   said first fiber tip (1), said second fiber tip (2) and said third fiber tip (3) are configured such that light emitted therefrom substantially overlaps and is substantially unfocused at an intended distance of the object (122) from said first, second, and third fiber tips (1, 2, 3); whereby:
   said first, second, and third fiber tips (1, 2, 3) are enabled to probe more closely to the object (122) than would be possible if the light emitted therefrom were to be focused on a single focal spot of the object (122).

9. The apparatus of claim 5, wherein:
said first fiber tip (1), said second fiber tip (2) and said third fiber tip (3) are configured such that light emitted therefrom substantially overlaps and is substantially unfocused at an intended distance of the object (122) from said first, second, and third fiber tips (1, 2, 3); whereby:
said first, second, and third fiber tips (1, 2, 3) are enabled to probe more closely to the object (122) than would be possible if the light emitted therefrom were to be focused on a single focal spot of the object (122).

10. The apparatus of claim 7, wherein:
said first fiber tip (1), said second fiber tip (2) and said third fiber tip (3) are configured such that light emitted therefrom substantially overlaps and is substantially unfocused at an intended distance of the object (122) from said first, second, and third fiber tips (1, 2, 3); whereby:
said first, second, and third fiber tips (1, 2, 3) are enabled to probe more closely to the object (122) than would be possible if the light emitted therefrom were to be focused on a single focal spot of the object (122).

11. The apparatus of claim 5, said non-linear light processing system (108) comprising a signal intensity multiplier multiplying the light intensities.

12. The apparatus of claim 5, said non-linear light processing system (108) comprising a photo detector outputting an electric signal proportional to at least said second power of the light intensities.

13. The apparatus of claim 5, said non-linear light processing system (108) comprising a digital processor processing the light intensities.

14. The apparatus of claim 7, said non-linear light processing system (108) comprising a signal intensity multiplier multiplying the light intensities.

15. The apparatus of claim 7, said non-linear light processing system (108) comprising a photo detector outputting an electric signal proportional to at least said third power of the light intensities.

16. The apparatus of claim 7, said non-linear light processing system (108) comprising a digital processor processing the light intensities.

17. The apparatus of claim 2, further comprising:
a fourth collection optical fiber (204), comprising a fourth fiber tip (4) thereof residing substantially in said fiber tip plane (71), optically connected with an object optical path (109) of said apparatus.

18. The apparatus of claim 4, further comprising:
a fourth optical collection fiber (204), comprising a fourth fiber tip (4) thereof residing substantially in said fiber tip plane (71), optically connected with said object optical path (109).

19. The apparatus of claim 18:
said first optical fiber (201) comprising single mode fiber;
said second optical fiber (202) comprising single mode fiber;
said third optical fiber (203) comprising single mode fiber; and
said fourth optical fiber (204) comprising multi mode fiber.

20. The apparatus of claim 5, further comprising:
a fourth optical collection fiber (204), comprising a fourth fiber tip (4) thereof residing substantially in said fiber tip plane (71), optically connected with an object optical path (109) of said apparatus.

21. The apparatus of claim 20:
said first optical fiber (201) comprising single mode fiber;
said second optical fiber (202) comprising single mode fiber;
said third optical fiber (203) comprising single mode fiber; and
said fourth optical fiber (204) comprising multi mode fiber.

22. The apparatus of claim 7, further comprising:
a fourth optical collection fiber (204), comprising a fourth fiber tip (4) thereof residing substantially in said fiber tip plane (71), optically connected with said object optical path (109).

23. The apparatus of claim 22:
said first optical fiber (201) comprising single mode fiber;
said second optical fiber (202) comprising single mode fiber;
said third optical fiber (203) comprising single mode fiber; and
said fourth optical fiber (204) comprising multi mode fiber.

24. The apparatus of claim 22, wherein:
said first fiber tip (1), said second fiber tip (2) and said third fiber tip (3) are configured such that light emitted therefrom substantially overlaps and is substantially unfocused at an intended distance of the object (122) from said first, second, and third fiber tips (1, 2, 3); whereby:
said first, second, and third fiber tips (1, 2, 3) are enabled to probe more closely to the object (122) than would be possible if the light emitted therefrom were to be focused on a single focal spot of the object (122).

25. The apparatus of claim 2, further comprising:
at least one of said first optical fiber (201), said second optical fiber (202), and said third optical fiber (203) optically connected with an object optical path (109) of said apparatus.

26. The apparatus of claim 4, further comprising:
at least one of said first optical fiber (201), said second optical fiber (202), and said third optical fiber (203) optically connected with said object optical path (109).

27. The apparatus of claim 7, further comprising:
at least one of said first optical fiber (201), said second optical fiber (202), and said third optical fiber (203) optically connected with said object optical path (109).

28. The apparatus of claim 4, further comprising:
light input into said apparatus, split into said first optical fiber (201), said second optical fiber (202), said third optical fiber (203), and said reference optical path (107); and
light output from said apparatus, joined from said reference optical path (107) and said object optical path (109).

29. The apparatus of claim 4, further comprising:
light input into said apparatus, split into said reference optical path (107) and said object optical path (109); and
light output from said apparatus, joined from said first optical fiber (201), said second optical fiber (202), said third optical fiber (203), and said reference optical path (107).

30. The apparatus of claim 7, further comprising:
light input into said apparatus, split into said first optical fiber (201), said second optical fiber (202), said third optical fiber (203), and said reference optical path (107); and
light output from said apparatus, joined from said reference optical path (107) and said object optical path (109).

31. The apparatus of claim 7, further comprising:
light input into said apparatus, split into said reference optical path (107) and said object optical path (109); and
light output from said apparatus, joined from said first optical fiber (201), said second optical fiber (202), said third optical fiber (203), and said reference optical path (107).

32. The apparatus of claim 22, further comprising:
light input into said apparatus, split into said first optical fiber (201), said second optical fiber (202), said third optical fiber (203), and said reference optical path (107); and
light output from said apparatus, joined from said reference optical path (107) and said object optical path (109).

33. The apparatus of claim 22, further comprising:
light input into said apparatus, split into said reference optical path (107) and said object optical path (109); and
light output from said apparatus, joined from said first optical fiber (201), said second optical fiber (202), third optical fiber (203), and said reference optical path (107).

34. The apparatus of claim 5, said non-linear light processing system (108) further comprising:
at least two filters (152, 154) filtering around different central wavelengths, the light passed through said first modulator (230), said second modulator (232), and said third modulator (234), wherein:
light emerging from each of said at least two filters (152, 154) is measured substantially simultaneously and correlated, thereby providing an expanded spectral range for measurement, and redundant measurement with improved signal to noise ratio.

35. The apparatus of claim 34, said non-linear light processing system (108) further comprising a reference tap (156) tapping the light passed through said first modulator (230), said second modulator (232), and said third modulator (234), to reduce the effect of any possible light intensity instability.

36. The apparatus of claim 7, said non-linear light processing system (108) further comprising:
at least two filters (152, 154) filtering around different central wavelengths, the light passed through said first modulator (230), said second modulator (232), and said third modulator (234), wherein:
light emerging from each of said at least two filters (152, 154) is measured substantially simultaneously and correlated, thereby providing an expanded spectral range for measurement, and redundant measurement with improved signal to noise ratio.

37. The apparatus of claim 36, said non-linear light processing system (108) further comprising a reference tap (156) tapping the light passed through said first modulator (230), said second modulator (232), and said third modulator (234), to reduce the effect of any possible light intensity instability.

38. The apparatus of claim 5, further comprising:
light input into said apparatus from at least two light sources (110).

39. The apparatus of claim 38, said at least two light sources (110) comprising substantially identical wavelength spectra, wherein:
intensities of said two light sources (110) add incoherently; and
said light input thereby comprises a higher intensity equal to intensities of said at least two light sources (110).

40. The apparatus of claim 38, said at least two light sources (110) comprising different wavelength spectra, wherein:
said light input thereby comprises a wider spectrum than the separate spectra of said at least two light sources (110), resulting in shorter coherence length and improved spatial resolution.

41. The apparatus of claim 40, further comprising at least two light source modulators (191), each said light source modulator (191) modulating light from one of said at least two light sources (110).

42. The apparatus of claim 7, further comprising:
light input into said apparatus from at least two light sources (110).

43. The apparatus of claim 42, said at least two light sources (110) comprising substantially identical wavelength spectra, wherein:
intensities of said two light sources (110) add incoherently; and
said light input thereby comprises a higher intensity equal to intensities of said at least two light sources (110).

44. The apparatus of claim 42, said at least two light sources (110) comprising different wavelength spectra, wherein:
said light input thereby comprises a wider spectrum than the separate spectra of said at least two light sources (110), resulting in shorter coherence length and improved spatial resolution.

45. The apparatus of claim 44, further comprising at least two light source modulators (191), each said light source modulator (191) modulating light from one of said at least two light sources (110).

46. An optical coherence tomography apparatus, comprising:
a first optical fiber (201), comprising a first fiber tip (1) thereof;
a second optical fiber (202), comprising a second fiber tip (2) thereof displaced from said first fiber tip (1) substantially in a fiber tip plane (71) substantially normal to an optical axis (72) of said apparatus;
a third optical fiber (203), comprising a third fiber tip (3) thereof displaced from said first fiber tip (1) and said second fiber tip (2) substantially in said fiber tip plane (71), such that said first fiber tip (1), second fiber tip (2) and third fiber tip (3) define said fiber tip plane (71);
a first modulator (230) for modulation of light passed through said first optical fiber (201);
a second modulator (232) for modulation of light passed through said second optical fiber (202);
a third modulator (234) for modulation of light passed through said third optical fiber further (203); and
a non-linear light processing system (108) of at least of second power with respect to an intensity of light passed through said first modulator (230), said second modulator (232), and said third modulator (234), thereby producing a localized, 2-dimensional instrumental function; wherein
not counting any collection fibers (204), said apparatus consists of no more optical fibers than said three optical fibers for said scanning through a 2-dimensional plane parallel to said fiber tip plane (71).

47. The apparatus of claim 46, further comprising:
a reference optical path (107);
a fourth modulator (236) for modulation of light passed through said reference optical path (107); and
said non-linear light processing system (108) of at least of third power with respect to an intensity of light passed through said first modulator (230), said second modulator (232), said third modulator (234), and said fourth modulator (236), thereby producing a localized, 3-dimensional instrumental function.

48. A probe head (270) apparatus for use in connection with an optical coherence tomography apparatus, comprising:
a first optical fiber (201), comprising a first fiber tip (1) thereof;
a second optical fiber (202), comprising a second fiber tip (2) thereof displaced from said first fiber tip (1) substantially in a fiber tip plane (71) substantially normal to an optical axis (72) of said probe head (270);

a third optical fiber (203), comprising a third fiber tip (3) thereof displaced from said first fiber tip (1) and said second fiber tip (2) substantially in said fiber tip plane (71), such that said first fiber tip (1), second fiber tip (2) and third fiber tip (3) define said fiber tip plane (71); and an optical connector (272) for connecting said probe head (270) to and disconnecting said probe head (270) from, said optical coherence tomography apparatus; wherein not counting any collection fibers (204), said probe head consists of no more optical fibers than said three optical fibers.

49. The probe head (270) apparatus of claim 48, wherein:
said first fiber tip (1), said second fiber tip (2) and said third fiber tip (3) are configured such that light emitted therefrom substantially overlaps and is substantially unfocused at an intended distance of an object (122) to be scanned from said first, second, and third fiber tips (1, 2, 3).

50. The probe head (270) apparatus of claim 48, further comprising:
a fourth optical collection fiber (204), comprising a fourth fiber tip (4) thereof residing substantially in said fiber tip plane (71), wherein:
said fourth fiber tip (4) is configured to receive light backscattered from the object (122).

51. The probe head (270) apparatus of claim 49, further comprising:
a fourth optical collection fiber (204), comprising a fourth fiber tip (4) thereof residing substantially in said fiber tip plane (71), wherein:
said fourth fiber tip (4) is configured to receive light backscattered from the object (122).

52. The probe head (270) apparatus of claim 50:
said first optical fiber (201) comprising single mode fiber;
said second optical fiber (202) comprising single mode fiber;
said third optical fiber (203) comprising single mode fiber; and
said fourth optical fiber (204) comprising multi mode fiber.

53. The probe head (270) apparatus of claim 51:
said first optical fiber (201) comprising single mode fiber;
said second optical fiber (202) comprising single mode fiber;
said third optical fiber (203) comprising single mode fiber; and
said fourth optical fiber (204) comprising multi mode fiber.

54. The probe head (270) apparatus of claim 49, further comprising:
beveling on at least two of said first, second, and third optical fibers (201, 202, 203), causing the light emitted therefrom to substantially overlap at said intended distance of the object (122).

55. The probe head (270) apparatus of claim 51, further comprising:
beveling on at least two of said first, second, and third optical fibers (201, 202, 203) causing the light emitted therefrom to substantially overlap at said intended distance of the object (122).

56. The probe head (270) apparatus of claim 49, further comprising:
a probe head tip refractory element (262) causing the light emitted from said first, second, and third optical fibers (201, 202, 203) to substantially overlap at said intended distance of the object (122).

57. The probe head (270) apparatus of claim 51, further comprising:
a probe head tip refractory element (262) causing the light emitted from said first, second, and third optical fibers (201, 202, 203) to substantially overlap at said intended distance of the object (122).

58. The probe head (270) apparatus of claim 57, further comprising:
a pellet connected to said fourth fiber tip (4) between said fourth fiber tip (4) and said probe head tip refractory element (262).

59. An optical coherence tomography method, using an optical coherence tomography apparatus therefor, comprising the steps of:
providing a first optical fiber (201), comprising a first fiber tip (1) thereof;
providing a second optical fiber (202), comprising a second fiber tip (2) thereof displaced from said first fiber tip (1) substantially in a fiber tip plane (71) substantially normal to an optical axis (72) of said apparatus; and:
scanning an object (122) in a one-dimensional direction parallel to the displacement between said first fiber tip (1) and said second fiber tip (2) by adjusting a relative phase delay $\phi_x$ (102) between said first optical fiber (201) and said second optical fiber (202); and
not counting any collection fibers (204), scanning in said direction parallel to said displacement between said first fiber tip (1) and said second fiber tip (2) using no more optical fibers than said two optical fibers.

60. The method of claim 59, further comprising the steps of:
providing a third optical fiber (203), comprising a third fiber tip (3) thereof displaced from said first fiber tip (1) and said second fiber tip (2) substantially in said fiber tip plane (71), such that said first fiber tip (1), second fiber tip (2) and third fiber tip (3) define said fiber tip plane (71);
scanning the object (122) in a direction parallel to the displacement between said first fiber tip (1) and said third fiber tip (3) by adjusting a relative phase delay $\phi_y$ (104) between said first optical fiber (201) and said third optical fiber (203); and
not counting any collection fibers (204), scanning through a 2-dimensional plane parallel to said fiber tip plane (71) using no more optical fibers than said three optical fibers; whereby:
scanning of the object (122) through said 2-dimensional plane parallel to said fiber tip plane (71) is enabled by said adjusting said phase delay $\phi_x$ (102) in combination with said adjusting said phase delay $\phi_y$ (104).

61. The method of claim 59, further comprising the step of:
scanning the object (122) in a direction substantially parallel to the optical axis (72) by adjusting a relative phase delay $\phi_z$ (106) between a reference optical path (107) and an object optical path (109) of said apparatus; whereby:
scanning of the object (122) through a 2-dimensional plane defined by the displacement between said first fiber tip (1) and said second fiber tip (2), and the optical axis (72) is enabled by said adjusting said phase delay $\phi_x$ (102) in combination with said adjusting said phase delay $\phi_z$ (106).

62. The method of claim 60, further comprising the step of:
scanning the object (122) in a direction substantially parallel to the optical axis (72) by adjusting a relative phase delay $\phi_z$ (106) between a reference optical path (107) and an object optical path (109) of said apparatus; whereby:

scanning of the object (122) through a 3-dimensional volume is enabled by said adjusting said phase delay $\phi_x$ (102) in combination with said adjusting said phase delay $\phi_y$ (104) in further combination with said adjusting said phase delay $\phi_z$ (106).

63. The method of claim 60, further comprising the steps of:

modulating light passed through said first optical fiber (201) with a first modulation (230);

modulating light passed through said second optical fiber (202) with a second modulation (232);

modulating light passed through said third optical fiber further (203) with a third modulation (234); and producing a localized, 2-dimensional instrumental function by non-linearly processing (108) to at least a second power with respect to intensity, light from said first modulation (230), said second modulation (232), and said third modulation (234).

64. The method of claim 61, further comprising the steps of:

modulating light passed through said first optical fiber (201) with a first modulation (230);

modulating light passed through said second optical fiber (202) with a second modulation (232);

modulating light passed through said reference optical path (107) with a fourth modulation (236); and producing a localized, 2-dimensional instrumental function by non-linearly processing (108) to at least a second power with respect to intensity, light from said first modulation (230), said second modulation (232), and said fourth modulation (232).

65. The method of claim 62, further comprising the steps of:

modulating light passed through said first optical fiber (201) with a first modulation (230);

modulating light passed through said second optical fiber (202) with a second modulation (232);

modulating light passed through said third optical fiber further (203) with a third modulation (234);

modulating light passed through said reference optical path (107) with a fourth modulation (236); and producing a localized, 3-dimensional instrumental function by non-linearly processing (108) to at least a third power with respect to intensity, light from said first modulation (230), said second modulation (232), said third modulation (234), and said fourth modulation (232).

66. The method of claim 60, further comprising the step of:

configuring said first fiber tip (1), said second fiber tip (2) and said third fiber tip (3) for overlapping light emitted therefrom substantially overlaps and is substantially unfocused at an intended distance of the object (122) from said first, second, and third fiber tips (1, 2, 3); whereby:

probing is enabled more closely to the object (122) with said first, second, and third fiber tips (1, 2, 3) than would be possible by focusing the light emitted therefrom on a single focal spot of the object (122).

67. The method of claim 63, further comprising the step of:

configuring said first fiber tip (1), said second fiber tip (2) and said third fiber tip (3) for overlapping light emitted therefrom substantially overlaps and is substantially unfocused at an intended distance of the object (122) from said first, second, and third fiber tips (1, 2, 3); whereby:

probing is enabled more closely to the object (122) with said first, second, and third fiber tips (1, 2, 3) than would be possible by focusing the light emitted therefrom on a single focal spot of the object (122).

68. The method of claim 65, further comprising the step of:

configuring said first fiber tip (1), said second fiber tip (2) and said third fiber tip (3) for overlapping light emitted therefrom substantially overlaps and is substantially unfocused at an intended distance of the object (122) from said first, second, and third fiber tips (1, 2, 3); whereby:

probing is enabled more closely to the object (122) with said first, second, and third fiber tips (1, 2, 3) than would be possible by focusing the light emitted therefrom on a single focal spot of the object (122).

69. The method of claim 63, said step of non-linearly processing (108) comprising multiplying the light intensities.

70. The method of claim 63, said step of non-linearly processing (108) comprising outputting an electric signal proportional to at least said second power of the light intensities, using a photo detector.

71. The method of claim 63, said step of non-linearly processing (108) comprising digitally processing the light intensities.

72. The method of claim 65, said step of non-linearly processing (108) comprising multiplying the light intensities.

73. The method of claim 65, said step of non-linearly processing (108) comprising outputting an electric signal proportional to at least said second power of the light intensities, using a photo detector.

74. The method of claim 65, said step of non-linearly processing (108) comprising digitally processing the light intensities.

75. The method of claim 60, further comprising the steps of:

providing a fourth collection optical fiber (204), comprising a fourth fiber tip (4) thereof residing substantially in said fiber tip plane (71); and optically connecting said fourth optical fiber (204) with an object optical path (109) of said apparatus.

76. The method of claim 62, further comprising the steps of:

providing a fourth collection optical fiber (204), comprising a fourth fiber tip (4) thereof residing substantially in said fiber tip plane (71); and optically connecting said fourth optical fiber (204) with an object optical path (109) of said apparatus.

77. The method of claim 76, wherein:

said first optical fiber (201) comprises single mode fiber;

said second optical fiber (202) comprises single mode fiber;

said third optical fiber (203) comprises single mode fiber; and said fourth optical fiber (204) comprises multi mode fiber.

78. The method of claim 63, further comprising the steps of:

providing a fourth optical collection fiber (204), comprising a fourth fiber tip (4) thereof residing substantially in said fiber tip plane (71); and optically connecting said fourth optical fiber (204) with an object optical path (109) of said apparatus.

79. The method of claim 78, wherein:
said first optical fiber (201) comprises single mode fiber;
said second optical fiber (202) comprises single mode fiber;
said third optical fiber (203) comprises single mode fiber; and
said fourth optical fiber (204) comprises multi mode fiber.

80. The method of claim 65, further comprising the steps of:
providing a fourth optical collection fiber (204), comprising a fourth fiber tip (4) thereof residing substantially in said fiber tip plane (71); and
optically connecting said fourth optical fiber (204) with an object optical path (109) of said apparatus.

81. The method of claim 80, wherein:
said first optical fiber (201) comprises single mode fiber;
said second optical fiber (202) comprises single mode fiber;
said third optical fiber (203) comprises single mode fiber; and
said fourth optical fiber (204) comprises multi mode fiber.

82. The method of claim 80, further comprising the step of:
configuring said first fiber tip (1), said second fiber tip (2) and said third fiber tip (3) for overlapping light emitted therefrom substantially overlaps and is substantially unfocused at an intended distance of the object (122) from said first, second, and third fiber tips (1, 2, 3); whereby:
probing is enabled more closely to the object (122) with said first, second, and third fiber tips (1, 2, 3) than would be possible by focusing the light emitted therefrom on a single focal spot of the object (122).

83. The method of claim 60, further comprising the step of:
providing at least one of said first optical fiber (201), said second optical fiber (202), and said third optical fiber (203) optically connected with an object optical path (109) of said apparatus.

84. The method of claim 62, further comprising the step of:
providing at least one of said first optical fiber (201), said second optical fiber (202), and said third optical fiber (203) optically connected with said object optical path (109).

85. The method of claim 65, further comprising the step of:
providing at least one of said first optical fiber (201), said second optical fiber (202), and said third optical fiber (203) optically connected with said object optical path (109).

86. The method of claim 62, further comprising the steps of:
splitting light input into said apparatus, into said first optical fiber (201), said second optical fiber (202), said third optical fiber (203), and said reference optical path (107); and
joining light output from said apparatus, from said reference optical path (107) and said object optical path (109).

87. The method of claim 62, further comprising the steps of:
splitting light input into said apparatus, into said reference optical path (107) and said object optical path (109); and
joining light output from said apparatus, from said first optical fiber (201), said second optical fiber (202), said third optical fiber (203), and said reference optical path (107).

88. The method of claim 65, further comprising the steps of:
splitting light input into said apparatus, into said first optical fiber (201), said second optical fiber (202), said third optical fiber (203), and said reference optical path (107); and
joining light output from said apparatus, from said reference optical path (107) and said object optical path (109).

89. The method of claim 65, further comprising the steps of:
splitting light input into said apparatus, into said reference optical path (107) and said object optical path (109); and
joining light output from said apparatus, from said first optical fiber (201), said second optical fiber (202), said third optical fiber (203), and said reference optical path (107).

90. The method of claim 80, further comprising the steps of:
splitting light input into said apparatus, into said first optical fiber (201), said second optical fiber (202), said third optical fiber (203), and said reference optical path (107); and
joining light output from said apparatus, from said reference optical path (107) and said object optical path (109).

91. The method of claim 80, further comprising the steps of:
splitting light input into said apparatus, into said reference optical path (107) and said object optical path (109); and
joining light output from said apparatus, from said first optical fiber (201), said second optical fiber (202), said third optical fiber (203), and said reference optical path (107).

92. The method of claim 63, said step of non-linearly processing (108) further comprising the steps of:
filtering around at least two different central wavelengths (152, 154), the light passed through said first modulator (230), said second modulator (232), and said third modulator (234); and
providing an expanded spectral range for measurement, and redundant measurement with improved signal to noise ratio, by measuring substantially simultaneously and correlating the filtered (152, 154) light.

93. The method of claim 92, said step of non-linearly processing (108) further comprising the step of:
reducing the effect of any possible light intensity instability by tapping (156) the light passed through said first modulator (230), said second modulator (232), and said third modulator (234).

94. The method of claim 65, said step of non-linearly processing (108) further comprising the steps of:
filtering around at least two different central wavelengths (152, 154), the light passed through said first modulator (230), said second modulator (232), and said third modulator (234); and
providing an expanded spectral range for measurement, and redundant measurement with improved signal to noise ratio, by measuring substantially simultaneously and correlating the filtered (152, 154) light.

95. The method of claim 94, said step of non-linearly processing (108) further comprising the step of:
reducing the effect of any possible light intensity instability by tapping the light passed through said first modulator (230), said second modulator (232), and said third modulator (234).

96. The method of claim 63, further comprising the step of:
inputting light into said apparatus from at least two light sources (110).

97. The method of claim 96, said at least two light sources (110) comprising substantially identical wavelength spectra, said light input thereby comprising a higher intensity equal to the intensity of said at least two light sources (110) by adding incoherently, intensities of said two light sources (110).

98. The method of claim 96, the light input from said at least two light sources (110) comprising different wavelength spectra, said light input thereby comprising a wider spectrum than the separate spectra of said at least two light sources (110), resulting in shorter coherence length and improved spatial resolution.

99. The method of claim 98, further comprising the step of:
light source modulating (191) modulating light from each of said at least two light sources (110).

100. The method of claim 65, further comprising the step of:
inputting light into said apparatus from at least two light sources (110).

101. The method of claim 100, said at least two light sources (110) comprising substantially identical wavelength spectra, said light input thereby comprising a higher intensity equal to the intensity of said at least two light sources (110) by adding incoherently, intensities of said two light sources (110).

102. The method of claim 100, the light input from said at least two light sources (110) comprising different wavelength spectra, said light input thereby comprising a wider spectrum than the separate spectra of said at least two light sources (110), resulting in shorter coherence length and improved spatial resolution.

103. The method of claim 102, further comprising the step of:
light source modulating (191) modulating light from each of said at least two light sources (110).

104. An optical coherence tomography method, using an optical coherence tomography apparatus therefor, comprising the steps of:
providing a first optical fiber (201), comprising a first fiber tip (1) thereof;
providing a second optical fiber (202), comprising a second fiber tip (2) thereof displaced from said first fiber tip (1) substantially in a fiber tip plane (71) substantially normal to an optical axis (72) of said apparatus;
providing a third optical fiber (203), comprising a third fiber tip (3) thereof displaced from said first fiber tip (1) and said second fiber tip (2) substantially in said fiber tip plane (71), such that said first fiber tip (1), second fiber tip (2) and third fiber tip (3) define said fiber tip plane (71);
modulating light passed through said first optical fiber (201) with a first modulation (230);
modulating light passed through said second optical fiber (202) with a second modulation (232);
modulating light passed through said third optical fiber further (203) with a third modulation (234); producing a localized, 2-dimensional instrumental function by non-linearly processing (108) to at least a second power with respect to intensity, light from said first modulation (230), said second modulation (232), and said third modulation (234); and
not counting any collection fibers (204), scanning through a 2-dimensional plane parallel to said fiber tip plane (71) using no more optical fibers than said three optical fibers.

105. The method of claim 104, further comprising the steps of:
modulating light passed through a reference optical path (107) of said apparatus with a fourth modulation (236); and
producing a localized, 3-dimensional instrumental function by non-linearly processing (108) to at least a third power with respect to intensity, light from said first modulation (230), said second modulation (232), said third modulation (234), and said fourth modulation (232).

106. A method for using a probe head (270) apparatus in connection with an optical coherence tomography apparatus, comprising the steps of:
providing a first optical fiber (201) of said probe head (270), comprising a first fiber tip (1) thereof;
providing a second optical fiber (202) of said probe head (270), comprising a second fiber tip (2) thereof displaced from said first fiber tip (1) substantially in a fiber tip plane (71) substantially normal to an optical axis (72) of said probe head (270);
providing a third optical fiber (203) of said probe head (270), comprising a third fiber tip (3) thereof displaced from said first fiber tip (1) and said second fiber tip (2) substantially in said fiber tip plane (71), such that said first fiber tip (1), second fiber tip (2) and third fiber tip (3) define said fiber tip plane (71); and
connecting and disconnecting (272) said probe head (270) to and from said optical coherence tomography apparatus; wherein
not counting any collection fibers (204), said probe head consists of no more optical fibers than said three optical fibers.

107. The method of claim 106, further comprising the step of:
configuring said first fiber tip (1), said second fiber tip (2) and said third fiber tip (3) for overlapping light emitted therefrom substantially overlaps and is substantially unfocused at an intended distance of an object (122) to be scanned from said first, second, and third fiber tips (1, 2, 3).

108. The method of claim 106, further comprising the steps of:
providing a fourth optical collection fiber (204), comprising a fourth fiber tip (4) thereof residing substantially in said fiber tip plane (71), and
configuring said fourth fiber tip (4) to receive light backscattered from the object (122).

109. The method of claim 107, further comprising the steps of:
providing a fourth collection optical fiber (204), comprising a fourth fiber tip (4) thereof residing substantially in said fiber tip plane (71), and
configuring said fourth fiber tip (4) to receive light backscattered from the object (122).

110. The method of claim 108, wherein:
said first optical fiber (201) comprises single mode fiber;
said second optical fiber (202) comprises single mode fiber;
said third optical fiber (203) comprises single mode fiber; and
said fourth optical fiber (204) comprises multi mode fiber.

111. The method of claim 109, wherein:
said first optical fiber (201) comprises single mode fiber;
said second optical fiber (202) comprises single mode fiber;
said third optical fiber (203) comprises single mode fiber; and
said fourth optical fiber (204) comprises multi mode fiber.

112. The method of claim 107, further comprising the step of:
causing the light emitted therefrom to substantially overlap at said intended distance of the object (122) by beveling at least two of said first, second, and third optical fibers (201, 202, 203).

113. The method of claim 109, further comprising the step of:
causing the light emitted therefrom to substantially overlap at said intended distance of the object (122) by beveling at least two of said first, second, and third optical fibers (201, 202, 203).

114. The method of claim 107, further comprising the step of:
causing the light emitted from said first, second, and third optical fibers (201, 202, 203) to substantially at said intended distance of the object (122), using a probe head tip refractory element (262).

115. The method of claim 109, further comprising the step of:
causing the light emitted from said first, second, and third optical fibers (201, 202, 203) to substantially overlap at said intended distance of the object (122), using a probe head tip refractory element (262).

116. The method of claim 115, further comprising the step of:
connecting a pellet to said fourth fiber tip (4) between said fourth fiber tip (4) and said probe head tip refractory element (262).

* * * * *